US009463259B2

(12) United States Patent
Hanada

(10) Patent No.: US 9,463,259 B2
(45) Date of Patent: Oct. 11, 2016

(54) STERILIZING APPARATUS AND STERILIZING METHOD

(71) Applicants: CANON MARKETING JAPAN KABUSHIKI KAISHA, Tokyo (JP); ELK CORPORATION, Osaka (JP); KABUSHIKI KAISHA ELQUEST, Chiba (JP)

(72) Inventor: Yasushi Hanada, Chiba (JP)

(73) Assignees: ELK CORPORATION, Osaka (JP); CANON MARKETING JAPAN KABUSHIKI KAISHA, Tokyo (JP); KABUSHIKI KAISHA ELQUEST, Chiba (JP)

( * ) Notice: Subject to any disclaimer, the term of this patent is extended or adjusted under 35 U.S.C. 154(b) by 335 days.

(21) Appl. No.: 13/645,168

(22) Filed: Oct. 4, 2012

(65) Prior Publication Data

US 2013/0089461 A1    Apr. 11, 2013

(30) Foreign Application Priority Data

Oct. 6, 2011    (JP) ................................. 2011-222381

(51) Int. Cl.
*A61L 2/20* (2006.01)

(52) U.S. Cl.
CPC ............. *A61L 2/208* (2013.01); *A61L 2202/11* (2013.01); *A61L 2202/121* (2013.01); *A61L 2202/122* (2013.01)

(58) Field of Classification Search
CPC ............ A61L 2/16; A61L 2/20; A61L 2/208
USPC .............................. 422/28, 33, 292, 295, 298
See application file for complete search history.

(56) References Cited

U.S. PATENT DOCUMENTS

| | | | |
|---|---|---|---|
| 5,508,009 A * | 4/1996 | Rickloff et al. | 422/292 |
| 5,527,507 A * | 6/1996 | Childers et al. | 422/28 |
| 6,734,405 B2 * | 5/2004 | Centanni et al. | 219/628 |
| 7,201,869 B2 * | 4/2007 | Williams et al. | 422/28 |
| 2005/0095168 A1 * | 5/2005 | Centanni | A61L 2/07 422/3 |

FOREIGN PATENT DOCUMENTS

JP    4-3747 U    1/1992

* cited by examiner

*Primary Examiner* — Regina M Yoo
(74) *Attorney, Agent, or Firm* — Canon USA, Inc. IP Division

(57) ABSTRACT

A sterilizing apparatus provides a structure for feeding a sterilizer left in a vaporizing chamber configured to gasify the sterilizer, into a sterilizing chamber, to stimulate a sterilizing action while reducing waste of the sterilizer.
The sterilizing apparatus includes a first atmosphere opening valve configured to perform an opening/closing operation to control communication between the atmosphere and the vaporizing chamber for vaporizing the sterilizer before the sterilizer is injected into the sterilizing chamber, and after a sterilizing gas vaporized in the vaporizing chamber is injected into the sterilizing chamber by vacuuming the vaporizing chamber with a vacuum pump, the vaporizing chamber and the atmosphere communicate with each other when the first atmosphere opening valve is opened while the vaporizing chamber and the sterilizing chamber communicate with each other.

6 Claims, 16 Drawing Sheets

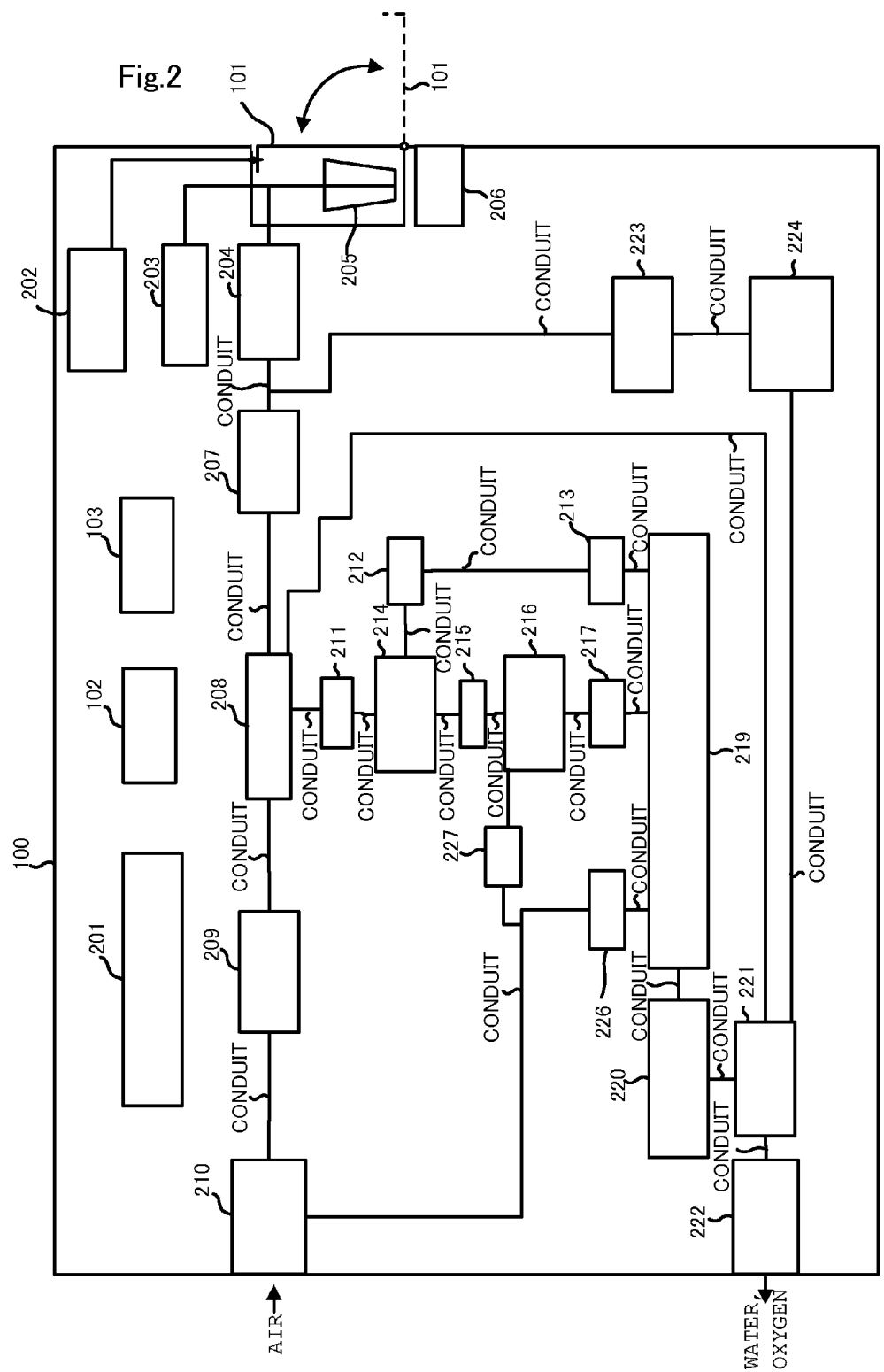

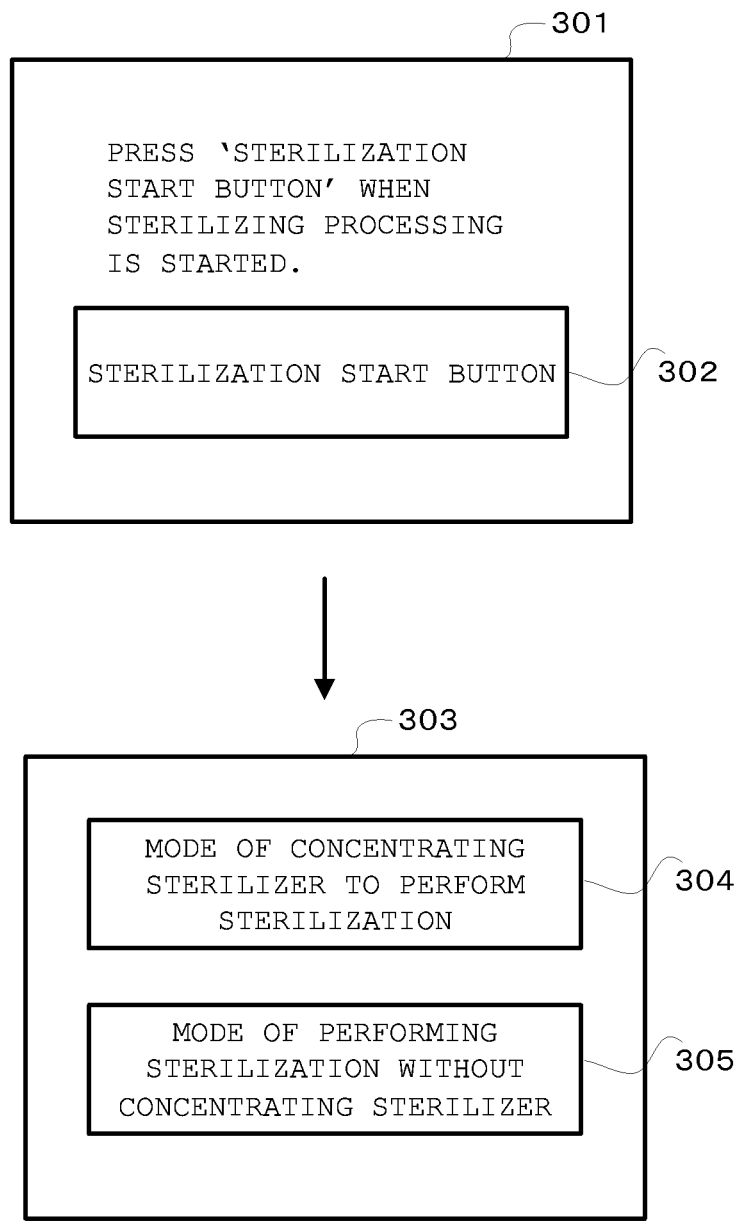

STERILIZING APPARATUS AND STERILIZING METHOD

BACKGROUND OF THE INVENTION

1. Field of the Invention

One disclosed aspect of the embodiments relates to a sterilizing apparatus and a sterilizing method. Particularly, one embodiment relates to a sterilizing apparatus which gasifies a sterilizer to feed the gasified sterilizer into a sterilizing chamber to perform sterilization, and a sterilizing method.

2. Description of the Related Art

Germs may be attached to medical instruments such as syringes or operation tools if the medical instruments are not sterilized after used, and may badly influence human bodies. Therefore, such instruments may not be reused. For this reason, sterilizing apparatuses for sterilizing an object such as a medical instrument, which needs to be sterilized, are used.

As an example of such a sterilizing apparatus, a sterilizing apparatus and a sterilizing method which sterilize an object by using hydrogen peroxide as a sterilizer are discussed (for example, Japanese Patent Application National Publication No. 8-505787).

Japanese Patent Application National Publication No. 8-505787 discusses a technique for injecting a sterilizer into a chamber and further injecting an inert gas into the chamber after a predetermined time elapses to further feed the sterilizer gas into a cavity, to sterilize the cavity even in a case where the object to be sterilized has the cavity.

However, Japanese Patent Application National Publication No. 8-505787 does not discuss how hydrogen peroxide vapor, which is the sterilizer, is produced, how the chamber which is a sterilizing chamber, is connected, and how the inert gas is injected.

SUMMARY OF THE INVENTION

One disclosed aspect of the embodiments is directed to a sterilizing apparatus which provides a structure for feeding a sterilizer left in a vaporizing chamber configured to gasify the sterilizer, into a sterilizing chamber, and stimulating a sterilizing action while reducing waste of the sterilizer.

One disclosed feature of the embodiments may be described as a process which is usually depicted as a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a program, a procedure, a method of manufacturing or fabrication, etc. One embodiment may be described by a schematic drawing depicting a physical structure. It is understood that the schematic drawing illustrates the basic concept and may not be scaled or depict the structure in exact proportions.

One embodiment is directed to a structure where the sterilizer may be strongly forced into a cavity by feeding the sterilizer left in the vaporizing chamber into the sterilizing chamber, and injecting the sterilizer into the sterilizing chamber and then increasing an amount of the atmosphere injected per predetermined time.

According to an aspect of the embodiments, a sterilizing apparatus for sterilizing an object according to an embodiment includes a sterilizing chamber which is a vacuum chamber for placing an object, a vaporizing chamber configured to vaporize a sterilizer before the sterilizer is injected into the sterilizing chamber, a vacuum device configured to vacuum the sterilizing chamber and the vaporizing chamber, and a first atmosphere opening valve configured to perform an opening/closing operation to control communication between the vaporizing chamber and the atmosphere, wherein after the sterilizer gas vaporized in the vaporizing chamber is injected into the sterilizing chamber by vacuuming the vaporizing chamber with the vacuum device, the vaporizing chamber and the atmosphere communicate with each other when the first atmosphere opening valve is opened while the vaporizing chamber and the sterilizing chamber communicate with each other.

According to another aspect of the embodiments, the sterilizing apparatus further includes a second atmosphere opening valve configured to perform an opening/closing operation to control communication between the sterilizing chamber and the atmosphere, and after the sterilizer gas vaporized in the vaporizing chamber is injected into the sterilizing chamber by vacuuming the vaporizing chamber with the vacuum device, the vaporizing chamber and the atmosphere communicate with each other when the first atmosphere opening valve is opened while the vaporizing chamber and the sterilizing chamber communicate with each other, and then the sterilizing chamber and the atmosphere communicate with each other when the second atmosphere opening valve is opened.

According to yet another aspect of the embodiments, the sterilizing apparatus further includes a second atmosphere opening valve configured to perform an opening/closing operation to control communication between the sterilizing chamber and the atmosphere, and after the sterilizer gas vaporized in the vaporizing chamber is injected into the sterilizing chamber by vacuuming the vaporizing chamber with the vacuum device, the vaporizing chamber and the atmosphere communicate with each other when the first atmosphere opening valve is opened while the vaporizing chamber and the sterilizing chamber communicate with each other, and the sterilizing chamber and the atmosphere communicate with each other when the second atmosphere opening valve is opened after a predetermined time.

According to yet another aspect of the embodiments, the sterilizing apparatus further includes a second atmosphere opening valve configured to perform an opening/closing operation to control communication between the sterilizing chamber and the atmosphere, and after the sterilizer gas vaporized in the vaporizing chamber is injected into the sterilizing chamber by vacuuming the vaporizing chamber with the vacuum device, the vaporizing chamber and the atmosphere communicate with each other when the first atmosphere opening valve is opened while the vaporizing chamber and the sterilizing chamber communicate with each other, and the sterilizing chamber and the atmosphere communicate with each other when the second atmosphere opening valve is opened after a pressure in the sterilizing chamber reaches a predetermined pressure.

According to yet another aspect of the embodiments, in a series of processes, the sterilizer is vaporized in the vaporizing chamber in a first pressure reduction state brought out by vacuuming the vaporizing chamber with the vacuum device, and the sterilizer vaporized in the vaporizing chamber is injected into the sterilizing chamber in a second pressure reduction state, whose pressure is lower than that of the first pressure reduction state, brought out by vacuuming the sterilizing chamber with the vacuum device, and then the sterilizing chamber and the atmosphere communicate with each other, and wherein sterilizing processing is performed by repeating the series of processes a predetermined number of times, by starting vacuuming the vaporizing chamber with the vacuum device after a pressure of the sterilizing chamber reaches the atmospheric pressure while the sterilizing chamber communicates with the atmosphere. Further, the sterilizer is hydrogen peroxide.

According to yet another aspect of the embodiments, there is provided a sterilizing method in a sterilizing apparatus according to the embodiments including a sterilizing chamber which is a vacuum chamber for placing an object, a vaporizing chamber configured to vaporize a sterilizer before the sterilizer is injected into the sterilizing chamber, a vacuum device configured to vacuum the sterilizing chamber and the vaporizing chamber, and a first atmosphere opening valve configured to perform an opening/closing operation to control communication between the vaporizing chamber and the atmosphere, wherein after the sterilizer gas vaporized in the vaporizing chamber is injected into the sterilizing chamber by vacuuming the vaporizing chamber with the vacuum device, the vaporizing chamber and the atmosphere communicate with each other when the first atmosphere opening valve is opened while the vaporizing chamber and the sterilizing chamber communicate with each other.

Further features and aspects of the embodiments will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the embodiments and, together with the description, serve to explain the principles of the disclosure.

FIG. 2 is a view illustrating an example of a hardware configuration of a sterilizing apparatus according to an embodiment.

FIG. 3 is a view illustrating an example of a screen displayed on a display part of the sterilizing apparatus.

DESCRIPTION OF THE EMBODIMENTS

Various exemplary embodiments, features, and aspects of the disclosure will be described in detail below with reference to the drawings.

A sterilizing apparatus and a sterilizing method for sterilizing a sterilization object according to an embodiment will be described with reference to the accompanying drawings.

First, an appearance of the sterilizing apparatus according to an embodiment will be described with reference to FIG. 1.

Figure 1:
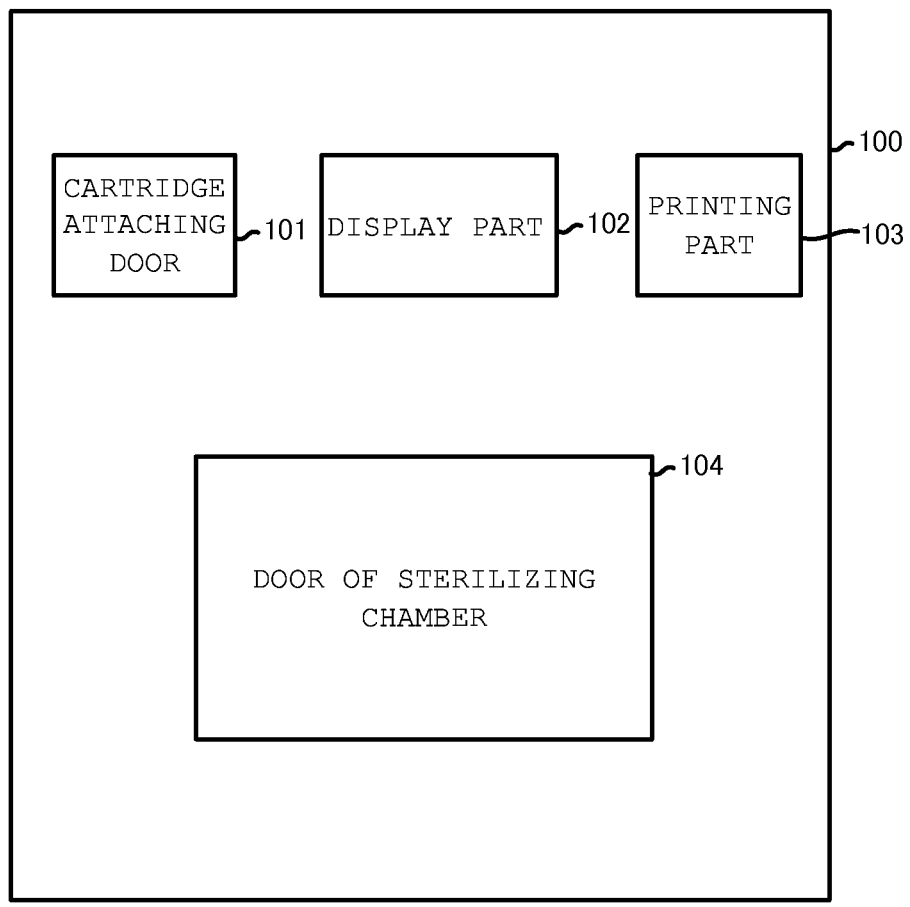
FIG. 1 is a view of an appearance of a sterilizing apparatus according to an embodiment when viewed from the front side.

FIG. 1 is a view of an appearance of a sterilizing apparatus according to an embodiment when viewed from the front side.

The sterilizing apparatus 100 according to an embodiment includes, a cartridge attaching door 101, a display part 102, a printing part 103, and a sterilizing chamber 104.

The cartridge attaching door 101 is a door for attaching a cartridge which is a container that is filled with a sterilizer (hydrogen peroxide or a hydrogen peroxide solution liquid). If the cartridge attaching door 101 is opened, a cartridge attaching position is found and a user may attach the cartridge thereto.

The display part 102 is a display screen of a touch panel such as a liquid crystal monitor.

The printing part 103 is a printer for printing a sterilization history or a sterilization result on a printing paper, and prints a sterilization history or a sterilization result on a printing paper as deemed appropriate.

The door 104 of the sterilizing chamber is a door for placing, for example, a sterilize target (sterilize object) such as a medical instrument therein to sterilize the sterilize object. If the door 104 of the sterilizing chamber is opened, the sterilizing chamber may be found. The sterilize target is placed in the sterilizing chamber and the door 104 of the sterilizing chamber is closed.

The sterilizing chamber is a casing having a predetermined capacity. An atmosphere (pressure) in the sterilizing chamber may be maintained in a range from the atmospheric pressure to a vacuum pressure. Further, a temperature in the sterilizing chamber is maintained within a predetermined range during sterilizing processing.

Next, an example of a hardware configuration of the sterilizing apparatus according to an embodiment will be described with reference to FIG. 2.

FIG. 2 is a view illustrating an example of a hardware configuration of a sterilizing apparatus according to an embodiment.

The sterilizing apparatus 100 according to an embodiment includes an operation processing unit (MPU and the like) 201, a display part 102, a printing part 103, a lock operation control part 202, an extraction needle operation control part 203, a cartridge attaching door 101, a liquid sensor 204, a cartridge 205, an RF-ID reader/writer 206, a liquid feeding rotary pump 207, a concentration furnace 208, a gas feeding/pressurizing pump 209, a gas suctioning HEPA filter 210, a valve (V1) 211, a valve (V3) 212, a valve (V4) 213, a measuring pipe 214, a valve (V2) 215, a vaporizing furnace 216, a valve (V5) 217, a valve (V9) 227, a valve (V7) 226, a sterilizing chamber (also referred to as a vacuum chamber) 219, a gas feeding vacuum pump 220, a gas exhausting HEPA filter 221, a sterilizer decomposing unit 222, a liquid feeding rotary pump 223, and a gas exhausting/evaporating furnace 224.

The calculation processing unit (an MPU and the like) 201 performs calculation processing and controls various hardware constituting the sterilizing apparatus 100.

The display part 102, the printing part 103, and the door 101 of the sterilizing chamber have already been described with reference to FIG. 1, and thus a detailed description thereof will be omitted.

The lock operation control part 202 is a part for locking/unlocking the cartridge attaching door 101. When the cartridge attaching door 101 is locked, the cartridge attaching door 101 is prevented from being opened, and when the cartridge attaching door 101 is unlocked, the cartridge attaching door 101 may be opened.

The cartridge 205 is a sealed container which is filled with a sterilizer (hydrogen peroxide or a hydrogen peroxide solution liquid). Further, an RF-ID storage medium is disposed at a lower side of the cartridge 205, and the storage medium stores a serial number as information for identifying the cartridge, a manufacturing date of the cartridge, a date and time (initial use date and time) when the cartridge is used in a sterilizing apparatus for the first time, and a remaining amount of the sterilizer filled in the cartridge.

The extraction needle operation control part 203 is apart for operating an extraction needle (syringe needle) for suctioning the sterilizer in the cartridge, which pricks an upper portion of the cartridge.

More specifically, when the extraction needle (syringe needle) for suctioning the sterilizer in the cartridge pricks from an upper portion of the cartridge, the extraction needle (syringe needle) is lowered toward the cartridge from the upper portion of the cartridge. Further, when the extraction needle (syringe needle) is withdrawn from the cartridge, the extraction needle (syringe needle) is raised to the upper portion of the cartridge.

The liquid sensor 204 is a unit for detecting whether the liquid sterilizer in the cartridge 205 is passing through a pipe (conduit) from the extraction needle (syringe needle), to the liquid feeding rotary pump 207 and the liquid feeding rotary pump 223. More specifically, it may be detected whether the sterilizer is passing through the pipe, from a spectrum obtained by irradiating the pipe with infrared ray.

The RF-ID reader/writer 206 is a unit for reading a serial number, a manufacturing date, an initial use time, and a remaining amount of sterilizer from an RF-ID disposed at a lower side of the cartridge 205. Further, the RF-ID reader/writer 206 is a unit for writing an initial use date and time and a remaining amount of a sterilizer in the RF-ID disposed at the lower side of the cartridge 205. In addition, the RF-ID reader/writer 206 is installed at a lower portion of a cartridge attaching position located behind the cartridge attaching door 101, and may read the RF-ID disposed at the lower side of the cartridge 205 and record data such as an initial use time, a remaining amount of sterilizer, and the like.

The liquid feeding rotary pump 207 is communicating with the concentration furnace 208 through a conduit and communicates with the liquid sensor 204 through a conduit. The liquid feeding rotary pump 207 is a unit for suctioning the liquid sterilizer in the cartridge 205 with a pump and sending the sterilizer to the concentration furnace 208 through a conduit. Further, the liquid feeding rotary pump 207 may suction a predetermined amount of a sterilizer from the cartridge 205 in association with the liquid sensor 204.

The concentration furnace 208 is communicating with the liquid feeding rotary pump 207, the gas feeding/pressurizing pump 209, the measuring pipe 214, and the gas exhausting HEPA filter 221 through conduits, respectively. As will be described below with reference to FIG. 10, the concentration furnace 208 heats the sterilizer fed through a conduit from the liquid feeding rotary pump 207 by using a heater, and evaporates (vaporizes) moisture and the like contained in the sterilizer and concentrates the sterilizer. Further, the vaporized water is forced out to a conduit communicating with the gas exhausting HEPA filter 221 by the air fed through a conduct from the gas feeding/pressurizing pump 209, and is exhausted from the concentration furnace 208. In addition, a valve (1) 211 is installed in a conduit between the measuring pipe 214 and the concentration furnace 208.

The gas feeding/pressurizing pump 209 is communicating with the concentration furnace 208 and the suctioning HEPA filter 210 through conduits, respectively. The gas feeding/pressurizing pump 209 is a unit for sending external air (atmosphere) outside the sterilizing apparatus 100 to the concentration furnace 208 communicating with the gas suctioning HEPA filter 210 through a conduit via the gas suctioning HEPA filter 210.

The gas suctioning HEPA filter 210 is communicating with the gas feeding/pressurizing pump 209, the sterilizing chamber 219, and the vaporizing furnace 216 through conduits, respectively. The gas suctioning HEPA filter 210 filters speck, dust, and germs in the external air (atmosphere) outside the sterilizing apparatus 100 with a high efficiency particulate air filter (HEPA filter) to clean air. Further, the cleaned air is sent to the concentration furnace 208 through a conduit by the gas feeding/pressurizing pump 209. In addition, the cleaned air communicates through a conduit with the vaporizing furnace 216 to be fed into the vaporizing furnace 216, or communicates through a conduit with the sterilizing chamber 219 to be fed into the sterilizing chamber 219. In other words, the gas suctioning HEAP filter 210 is communicating with the external air (atmosphere) outside the sterilizing apparatus 100. Accordingly, a conduit between the gas feeding/pressurizing pump 209 and the gas suctioning HEPA filter 210, a conduit between the sterilizing chamber 219 and the gas suctioning HEPA filter 210, and a conduit between the vaporizing furnace 216 and the gas suctioning HEPA filter 210 are communicating with the external air (atmosphere) via the gas suctioning HEPA filter 210.

Further, a valve (V9) 227 is installed in a conduit between the gas suctioning HEPA filter 210 and the vaporizing furnace 216. In addition, a valve (V7) 226 is installed in a conduit between the gas suctioning HEPA filter 210 and the sterilizing chamber 219.

The valve (V1) 211 is installed in a conduit between the concentration furnace 208 and the measuring pipe 214. When the valve (V1) 211 is opened, the concentration furnace 208 and the measuring pipe 214 communicates with each other through the conduit. When the valve is closed, the concentration furnace 208 and the sterilizing chamber 214 are prevented from communicating with each other through the conduit.

The valve (V3) 212 is installed in a conduit between the measuring pipe 214 and the sterilizing chamber 219. When the valve (V3) 212 is opened, the measuring pipe 214 and the sterilizing chamber 219 communicates with each other through the conduit. When the valve is closed, the measuring pipe 214 and the sterilizing chamber 219 are prevented from communicating with each other through the conduit. Further, the valve is installed around the measuring pipe 214, and is installed at a location closer to the measuring pipe 214 than at least the below-described valve V4.

The valve (V4) 213 is installed in a conduit between the measuring pipe 214 and the sterilizing chamber 219. When the valve (V4) 213 is opened, the measuring pipe 214 and the sterilizing chamber 219 communicates with each other through the conduit. When the valve is closed, the measuring pipe 214 and the sterilizing chamber 219 are prevented from communicating with each other through the conduit. Further, the valve is installed around the sterilizing chamber 219, and is installed at a location closer to the sterilizing chamber 219 than at least the below-described valve V3.

In the present exemplary embodiment, conduction through the conduit between the measuring pipe and the sterilizing chamber becomes possible or impossible by opening and closing the valve (V4) 213 and the valve (V3) 212. However, conduction through the conduit between the measuring pipe and the sterilizing chamber becomes possible or impossible by opening and closing one of the valve (V4) 213 and the valve (V3) 212.

More specifically, only one of the valve (V4) 213 and the valve (V3) 212 is provided and conduction through the conduit between the measuring pipe and the sterilizing chamber becomes possible or impossible by opening and closing either of the valves.

The measuring pipe 214 is communicating through conduits with the concentration furnace 208, the vaporizing furnace 216, and the sterilizing chamber 219.

The measuring pipe 214 opens the valve (V1) 211 to inject the sterilizer from the concentration furnace 208, and opening the valve (V3) 212 and the valve (V4) 213 to remove unnecessary air suctioned from the cartridge 205 and/or unnecessary air injected into the concentration furnace 208 from the gas suctioning HEPA filter 210 and then injected into the measuring pipe 214 from the concentration furnace 208. Details of the measuring pipe 214 will be described below with reference to FIG. 10.

The valve (V2) 215 is installed in a conduit between the measuring pipe 214 and the vaporizing furnace 216. When the valve is opened, the measuring pipe 214 and the vaporizing furnace 216 communicate with each other through the conduit. When the valve is closed, the measuring pipe 214 and the vaporizing furnace 216 are prevented from communicating with each other through the conduit.

The vaporizing furnace 216 is communicating through conduits with the measuring pipe 214, the gas suctioning HEPA filter 210, and the sterilizing chamber 219. The vaporizing furnace 216 is an application example of a vaporizing chamber of an embodiment. The vaporizing furnace 216 is a unit for reducing a pressure by the gas feeding vacuum pump 220 to vaporize the sterilizer before the sterilizer is injected into the sterilizing chamber.

The valve (V5) 217 is installed in a conduit between the vaporizing furnace 216 and the sterilizing chamber 219. When the valve is opened, the vaporizing furnace 216 and the sterilizing chamber 219 communicate with each other through the conduit. When the valve is closed, the vaporizing furnace 216 and the sterilizing chamber 219 are prevented from communicating with each other through the conduit.

The valve (V9) 227 (corresponding to a first atmosphere opening valve of an embodiment) is installed in a conduit between the vaporizing furnace 216 and the gas suctioning HEPA filter 210. When the valve is opened, the gas suctioning HEPA filter 210 and the vaporizing furnace 216 communicates with each other through the conduit. When the valve is closed, the preparation chamber 210 and the vaporizing furnace 216 are prevented from communicating with each other through the conduit. In other words, the valve (V9) 227 is capable of opening/closing the communication of the vaporizing furnace 216 and the external air (atmosphere).

The valve (V7) 226 is installed in a conduit between the sterilizing chamber 219 and the gas suctioning HEPA filter 210. When the valve is opened, the gas suctioning HEPA filter 210 and the sterilizing chamber 219 communicates with each other through the conduit. When the valve is closed, the gas suctioning HEPA filter 210 and the sterilizing chamber 219 are prevented from communicating with each other through the conduit. In other words, the valve (V7) 226 is capable of opening/closing the communication of the sterilizing chamber 219 and the external air (atmosphere).

As already described with reference to FIG. 1, the sterilizing chamber (also referred to as a vacuum chamber) 219 has a predetermined capacity for sterilizing a sterilize object, for example, a medical instrument and the like, and is a vacuum chamber for receiving an object. A pressure in the sterilizing chamber may be maintained in a range from the atmospheric pressure to a vacuum pressure. Further, a temperature in the sterilizing chamber is maintained at a temperature within a predetermined range during sterilizing processing. In addition, a pressure sensor is disposed in the sterilizing chamber 219, and a pressure (atmospheric pressure) in the sterilizing chamber 219 may be measured by the pressure sensor. The sterilizing apparatus 100 determines whether a pressure (atmospheric pressure) in the sterilizing chamber 219 is a predetermined atmospheric pressure by using the atmospheric pressure in the sterilizing chamber 219 measured by the pressure sensor.

The gas feeding vacuum pump 220 suctions the gas in the spaces in the sterilizing chamber 219, in the vaporizing furnace 216, in the measuring pipe 214, in a conduit between the measuring pipe 214 and the vaporizing furnace 216, in a conduit between the vaporizing furnace 116 and the sterilizing chamber 219, in a conduit between the measuring pipe 214 and the sterilizing chamber 219. The gas feeding vacuum pump 220 reduces the pressures within the spaces (a state in which the spaces are filled with a gas whose pressure is lower than the atmospheric pressure).

The gas feeding vacuum pump 220 is communicating with the sterilizing chamber 219 through a conduit, and is communicating with the gas exhausting HEPA filter 221 through a conduit.

The gas exhausting HEPA filter 221 is communicating with the gas feeding vacuum pump 220 through a conduit. Further, the gas exhausting HEPA filter 221 is communicating with the gas exhausting/evaporating furnace 224 through a conduit. In addition, the gas exhausting HEPA filter 221 is communicating with the sterilizer decomposing unit 222 through a conduit. Furthermore, the gas exhausting HEPA filter 221 is communicating with the concentration furnace 208 through a conduit.

The gas exhausting HEPA filter 221 filters the gas suctioned from the sterilizing chamber 219 by the gas feeding vacuum pump 220 to remove speck, dust, germs and the like in the gas sent through the conduct between the HEPA filter and the gas feeding vacuum pump 220 so that the suctioned gas is cleaned. Further, the cleaned gas is sent to the sterilizer decomposing unit 222 through a conduit between the sterilizer decomposing unit 222 and the gas exhausting HEPA filter 221. The molecules of the sterilizer contained in the gas are decomposed by the sterilizer decomposing unit 222, and the decomposed molecules are emitted to the outside of the sterilizing apparatus 100.

Further, the gas exhausting HEPA filter 221 cleans the gas exhausted from the concentration filter 208 though a conduit between the concentration furnace 208 and the gas exhausting HEPA filter 221. The gas is water obtained by heating and vaporizing the sterilizer but contains a finite amount of sterilizer, and thus is sent to the sterilizer decomposing unit 222 through a conduit between the sterilizer decomposing unit 222 and the gas exhausting HEPA filter 221. Then, the molecules of the sterilizer contained in the gas are decomposed by the sterilizer decomposing unit 222, and the decomposed molecules are discharged outside the sterilizing apparatus 100.

Further, the gas exhausting HEPA filter 221 cleans the evaporated sterilizer sent from the gas exhausting/evaporating furnace 224 through a conduit between the gas exhausting/evaporating furnace 224 and the gas exhausting HEPA filter 221. Then, the cleaned sterilizer (gas) is sent to the sterilizer decomposing unit 222 through a conduit between the sterilizer decomposing unit 222 and the gas exhausting HEPA filter 221, the molecules of the sterilizer contained in the gas are decomposed by the sterilizer decomposing unit 222, and the decomposed molecules are discharged outside the sterilizing apparatus 100.

The gas exhausting HEPA filter 221 cleans the gas sent through the conduit, so that dust or impurities is prevented from piling up in the sterilizer decomposing unit 222, which extends a product life of the sterilizer decomposing unit 222.

The sterilizer decomposing unit 222 is communicating with the gas exhausting HEPA filter 221 through a conduit. The sterilizer decomposing unit 222 decomposes the molecules of the sterilizer contained in the gas sent from the conduit between the sterilizer decomposing unit 222 and the gas exhausting HEPA filter 221, and emits the molecules produced by the decomposition, outside the sterilizing apparatus 100.

The sterilizer decomposing unit 222 is a unit for decomposing the sterilizer, and is capable of decomposing the evaporated hydrogen peroxide into water and oxygen by using manganese dioxide as a catalyst, for example, when the sterilizer is hydrogen peroxide or a hydrogen peroxide solution.

The liquid feeding rotary pump 223 is communicating with the gas exhausting/evaporating furnace 224 through a conduit and is communicating with the liquid sensor 204 through a conduit.

The liquid feeding rotary pump 223 suctions all the liquid sterilizer in the cartridge 205, and feeds all the sterilizer sent through the conduit between the liquid sensor 204 and the liquid feeding rotary pump 223 to the gas exhausting/evaporating furnace 224 through the conduit between the liquid feeding rotary pump 223 and the gas exhausting/evaporating furnace 224.

The gas exhausting/evaporating furnace 224 is communicating with the liquid feeding rotary pump 223 through a conduit and is communicating with the gas exhausting HEPA filter 221 through a conduit.

The gas exhausting/evaporating furnace 224 heats all the liquid sterilizer in the cartridge 205 which is sent through the conduit between the liquid feeding rotary pump 223 and the gas exhausting/evaporating furnace 224 with a heater disposed in the gas exhausting/evaporating furnace 224, and evaporates all the sterilizer. Further, the evaporated sterilizer is sent to the gas exhausting HEPA filter 221 through the conduit between the gas exhausting HEPA filter 221 and the gas exhausting/evaporating furnace 224.

Next, an example of processes of the sterilizing processing by the sterilizing apparatus according to the exemplary embodiment will be described with reference to FIGS. 4A and 4B.

Figure 4A:
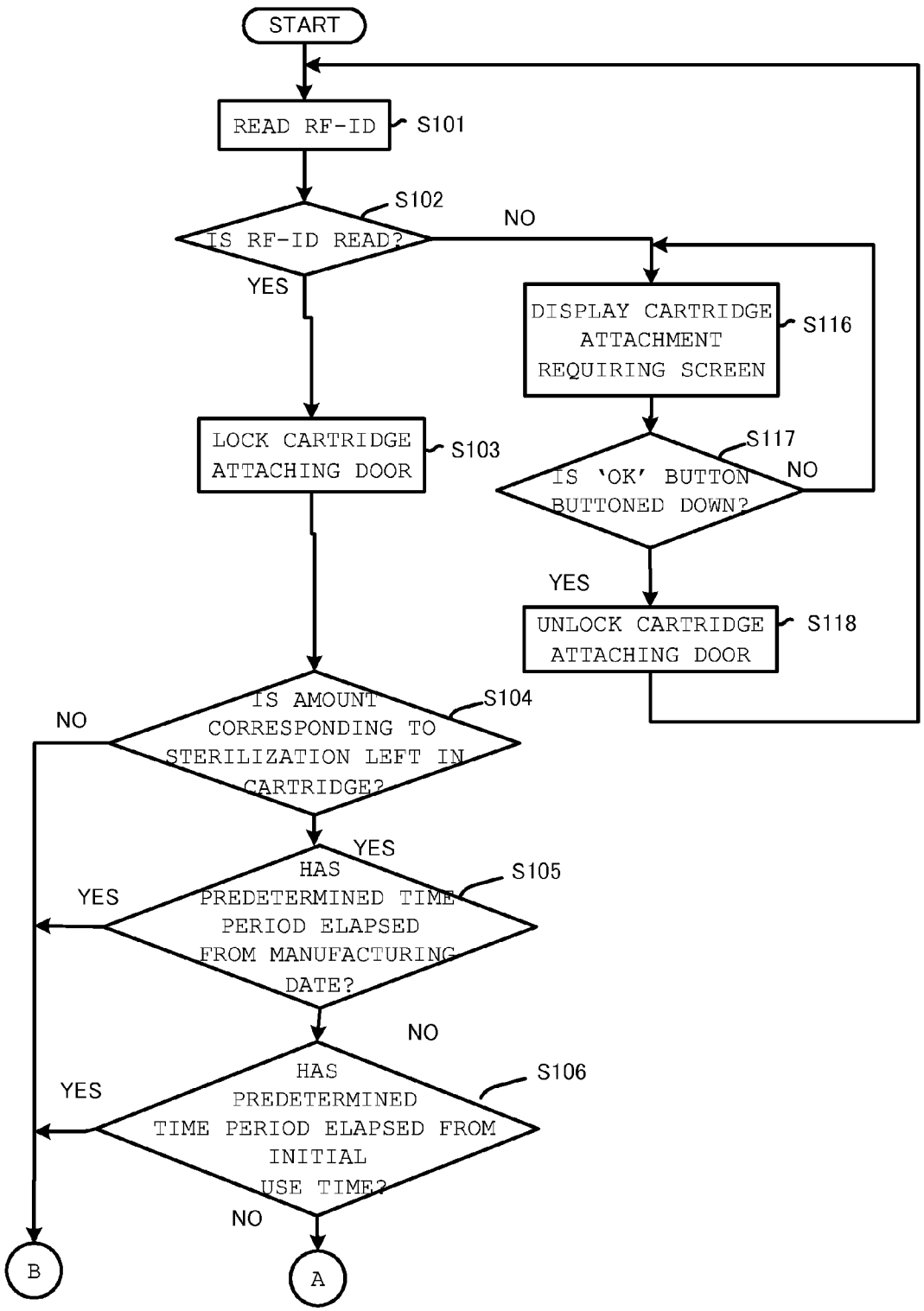
FIG. 4A is the first part of a flowchart illustrating an example of processes of sterilizing processing by the sterilizing apparatus according to an embodiment.
Figure 4B:
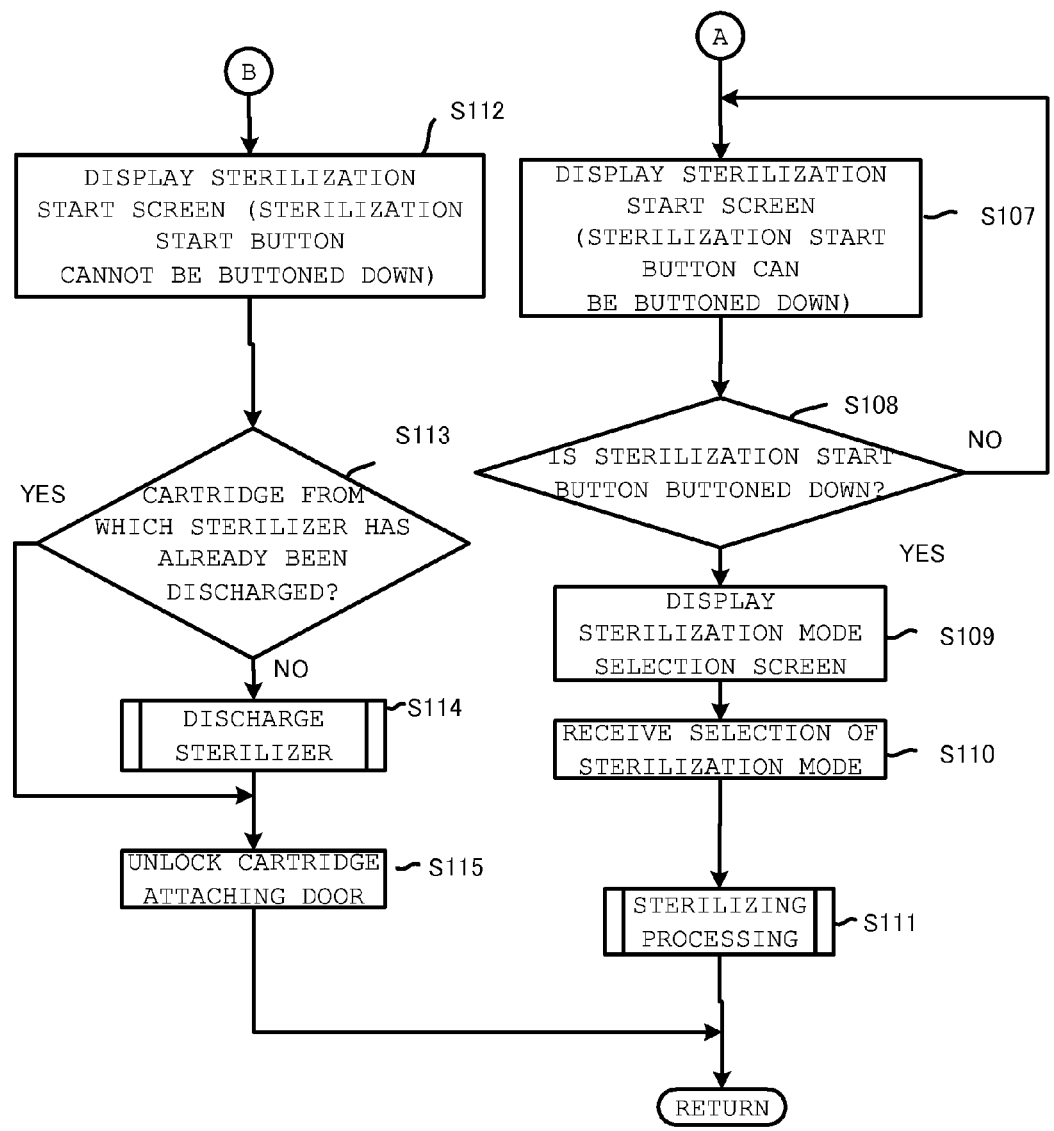
FIG. 4B is the second part of the flowchart illustrating an example of processes of sterilizing processing by the sterilizing apparatus according to an embodiment

The processes (processing) illustrated in FIGS. 4A and 4B are performed by controlling the operations of the units in the sterilizing apparatus with the operation processing unit 201 of the sterilizing apparatus 100.

More specifically, the processes (processing) illustrated in FIGS. 4A and 4B are performed by executing programs readable by the operation processing unit 201 of the sterilizing apparatus 100 to control the operations of the units.

FIG. 4A is the first part of a flowchart illustrating an example of processes of sterilizing processing by the sterilizing apparatus according to the exemplary embodiment.

In the sterilizing apparatus 100, if a power source is turned on, first, the RF-ID reader/writer 206 reads data from the RF-ID (storage medium) installed below the cartridge 205 in operation S101.

In operation S101, the data read from the RF-ID (storage medium) includes a serial number as information for identifying the cartridge, a manufacturing date of the cartridge, a date and time (initial use date and time) when the cartridge is used in a sterilizing apparatus for the first time, and a remaining amount of the sterilizer with which the cartridge is filled. In other words, a serial number, a manufacturing date, an initial user date and time, and a remaining amount of a sterilizer are stored in the RF-ID (storage medium) installed in the cartridge 205.

Next, when it is determined that data has been read from the RF-ID in operation S101 (YES in operation S102), the sterilizing apparatus 100 determines that the cartridge is installed at an attachment position of the cartridge in the sterilizing apparatus 100 and locks the cartridge attaching door 101 in operation S103.

Further, the sterilizing apparatus 100 determines whether a predetermined amount (for example, 8 milliliters) of sterilizer corresponding to one sterilization is present in the cartridge. More specifically, it is determined whether a remaining amount of a sterilizer acquired from the RF-ID is larger than the predetermined amount corresponding to one sterilization. In other words, when it is determined that the remaining amount of a sterilizer is larger than the predetermined amount corresponding to one sterilization, the predetermined amount of sterilizer corresponding to one sterilization is present in the cartridge (sufficient sterilizing processing may be performed) (YES in operation S104), and processing of operation S105 is performed. Meanwhile, when it is determined that the remaining amount of sterilizer is smaller than the predetermined amount corresponding to one sterilization, the predetermined amount of sterilizer corresponding to one sterilization is not present in the cartridge (sufficient sterilizing processing may not be performed) (NO in operation S104), processing of operation S112 is performed.

In operation S105, the sterilizing apparatus 100 determines whether a predetermined period (for example, 13 months) has elapsed from a manufacturing date of the cartridge acquired from the RF-ID.

When it is determined that a predetermined period has elapsed from the manufacturing date (YES in operation S105), it is determined that a sufficient sterilizing processing may not be performed and the process proceeds to continuation connector B where processing of operation S112 is performed (FIG. 4B). Meanwhile, when it is determined that a predetermined period has not elapsed from the manufacturing date (NO in operation S105), it is determined that sufficient sterilizing processing may be performed and processing of operation S106 is performed.

The sterilizing apparatus 100 determines whether a predetermined period (for example, 2 weeks) has elapsed from an initial use date and time acquired from the RF-ID in operation S106.

Further, when it is determined that a predetermined period (for example, 2 weeks) has elapsed from the initial use date and time acquired from the RF-ID (YES in operation S106), it is determined that sufficient sterilizing processing may not be performed and the process proceeds to continuation connector B which continues in FIG. 4B and where processing of operation S112 is performed (FIG. 4B). Meanwhile, when it is determined that a predetermined period (for example, 2 weeks) has not elapsed (NO in operation S106), it is determined that sufficient sterilizing processing may be performed and the process proceeds to continuation connector A which continues in FIG. 4B.

FIG. 4B is the second part of a flowchart illustrating an example of processes of sterilizing processing by the sterilizing apparatus according to the exemplary embodiment.

From continuation connector A, processing of operation S107 is performed.

In operation S107, the sterilizing apparatus 100 displays a sterilization start screen (301 in FIG. 3) on the display part 102.

FIG. 3 is a view illustrating an example of a screen displayed on the display part 102 of the sterilizing apparatus 100.

A 'sterilization start button' is displayed on the sterilization start screen 301. The 'sterilization start button' 302 on the sterilization start screen 301 displayed in operation S107 is enabled (activated) to be buttoned down by the user.

If the 'sterilization start button' 302 is buttoned down by the user (YES in operation S108), the sterilizing apparatus 100 displays the sterilizing mode selecting screen (303 in FIG. 3) on the display part 102.

A button 304 for a 'mode of concentrating a sterilizer to perform sterilization' and a button 305 for a 'mode of performing sterilization without concentrating a sterilizer' are displayed on the sterilizing mode selecting screen 303.

The sterilizing apparatus 100 receives a selection of one of the button 304 for a 'mode of concentrating a sterilizer to perform sterilization' and the button 305 for a 'mode of performing sterilization without concentrating a sterilizer' from the user in operation S110, and performs sterilizing processing (step S111) according to the mode of the button selected by the user. The details of the sterilizing processing (step S111) will be described below with reference to FIG. 5.

In this way, a mode of processing sterilization may be changed and used in one sterilizing apparatus according to an instruction of the user. More specifically, when the button 304 for a 'mode of concentrating a sterilizer to perform sterilization' is buttoned down by the user, the sterilizer is concentrated to perform the sterilizing processing, and when the button 305 for a 'mode of performing sterilization without concentrating a sterilizer' is button down, the sterilizing processing is performed without concentrating the sterilizer.

Then, when the sterilizing processing (step S111) is ended, the sterilizing apparatus 100 returns the processing to operation S101.

From continuation connector B, in operation S112, the sterilizing apparatus 100 displays a sterilization start screen (301 of FIG. 3) on the display part 102. However, the 'sterilization start button' 302 on the sterilization start screen (301 of FIG. 3) displayed in operation S112 may not be buttoned down by the user (the 'sterilization start button' 302 is not active). Accordingly, a sterilization starting instruction from the user may not be received.

Then, the sterilizing apparatus 100 determines in operation S113 whether the cartridge installed at an attachment position of the cartridge has already discharged the sterilizer, from the serial number acquired from the RF-ID in operation S101. More specifically, a serial number for identifying the cartridge from which the sterilizer has already been discharged is stored in the memory (storage part) in the sterilizing apparatus 100. Depending on whether the serial number acquired from the RF-ID in operation S101 coincides with the serial number stored in the memory (storage part), it is determined whether the cartridge currently attached to the sterilizing apparatus 100 is the cartridge from which the sterilizer has already been discharged.

When it is determined that the cartridge currently attached to the sterilizing apparatus 100 is a cartridge from which the sterilizer has already been discharged (YES in operation S113), processing of operation S115 is performed. Meanwhile, when it is determined that the cartridge is not a cartridge from which the sterilizer has already been discharged (NO in operation S113), a sterilizer discharging processing (step S114) for absorbing all the remaining amount of liquid sterilizer left in the cartridge, decomposing all the sterilizer, and discharging the decomposed sterilizer out of the sterilizing apparatus 100 is performed and then the processing of operation S115 is performed. The details of the sterilizer discharging processing of operation S114 will be described below with reference to FIG. 9.

If the processing of operation S114 is performed, the serial number read in operation S101 is stored in the memory (storage part) in the sterilizing apparatus 100 as a serial number for identifying the cartridge from which the sterilizer has already been discharged (discarded).

The sterilizing apparatus 100 unlocks the cartridge attaching door 101 in operation S115.

Figure 11:
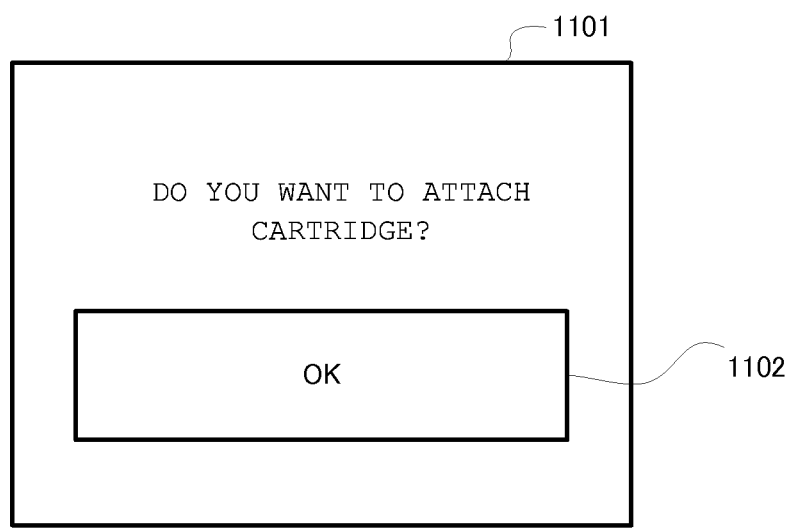
FIG. 11 is a view illustrating an example of a screen requesting to attach a cartridge displayed on a display part of the sterilizing apparatus.

When it is determined in operation S102 that data is not read from the RF-ID in operation S101 (NO in operation S102), the sterilizing apparatus 100 determines that a cartridge is not installed at an attachment position of the cartridge in the sterilizing apparatus 100 and displays a cartridge attachment requesting screen 1101 illustrated in FIG. 11 in operation S116.

FIG. 11 is a view illustrating an example of a cartridge attachment requesting screen 1101 displayed on a display part 102 of the sterilizing apparatus 100.

An 'OK' button 1102 is displayed on the cartridge attachment requesting screen 1101.

Further, the sterilizing apparatus 100 determines in operation S117 whether the 'OK' button 1102 of the cartridge attachment requesting screen 1101 is buttoned down by the user, and when the 'OK' button 1102 is buttoned down (YES in operation S117), the sterilizing apparatus 100 unlocks the cartridge attaching door 101 in operation S118 and returns the processing to operation S101. Meanwhile, when the 'OK' button 1102 is not buttoned down (NO in operation S117), the cartridge attachment requesting screen 1101 is continuously displayed.

The unlock and lock of the cartridge attaching door 101 is performed by an operation of the lock operation control part 202.

Next, an example of detailed processing of the sterilizing processing illustrated in S111 of FIG. 4B will be described with reference to FIG. 5.

Figure 5:
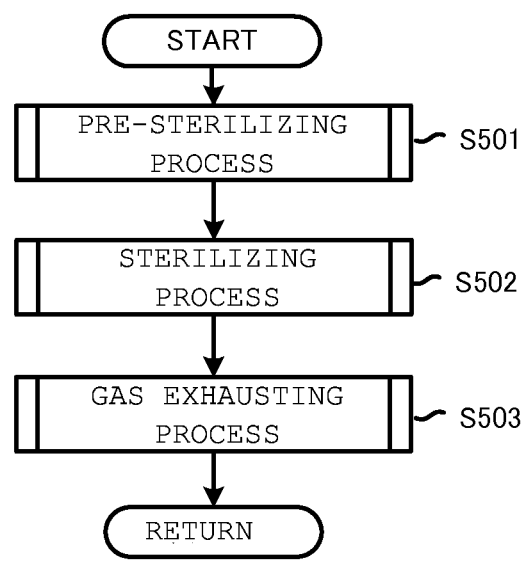
FIG. 5 is a view illustrating an example of detailed processing of the sterilizing illustrated in S111 of FIG. 4B.

FIG. 5 is a view illustrating the example of detailed processing of the sterilizing processing illustrated in S111 of FIG. 4B.

The processes (processing) illustrated in FIG. 5 are performed by the operation processing unit 201 of the sterilizing apparatus 100 which controls the operations of each device in the sterilizing apparatus.

In other words, the processes (processing) illustrated in FIG. 5 are performed by executing programs readable by the operation processing unit 201 of the sterilizing apparatus 100 to control the operations of each device.

When the process illustrated in operation S501 of FIG. 5 starts, all the valves (the valve (V1) 211, the valve (V2) 215, the valve (V3) 212, the valve (V4) 213, the valve (V9) 227, and the valve (V7) 226) of the sterilizing apparatus 100 are closed.

First, in operation S501, the sterilizing apparatus 100 performs processing of a pre-sterilizing process. The pre-sterilizing process includes operating the gas feeding vacuum pump 220, suctioning the gas in the sterilizing chamber 219, and reducing the pressure in the sterilizing chamber 219 to a predetermined atmosphere (for example, 45 Pa). The detailed processing of the processing of the pre-sterilizing process will be described below with reference to FIG. 6.

Further, in operation S502, the sterilizing apparatus 100 performs processing of a sterilizing process. The sterilizing process includes injecting the sterilizer into the sterilizing chamber 219 and sterilizing the sterilize object. The detailed processing of the processing of the sterilizing process will be described below with reference to FIGS. 7A through 7D.

Next, in operation S503, the sterilizing apparatus 100 performs processing of a ventilating process for removing the sterilizer contained in the sterilizing chamber 219 and the vaporizing furnace 216. The detailed processing of the processing of the ventilating process will be described below with reference to FIG. 8.

An example of detailed processing of a pre-sterilizing processing illustrated in S501 of FIG. 5 will be described with reference to FIG. 6.

Figure 6:
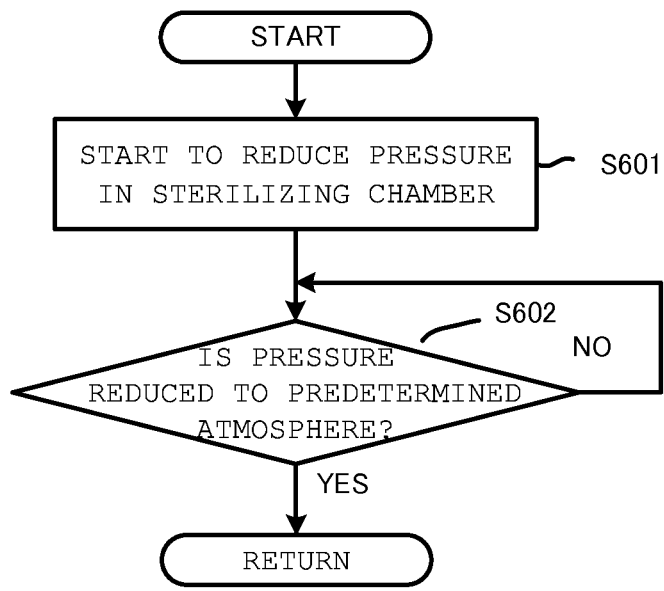
FIG. 6 is a view illustrating an example of detailed processing of pre-sterilizing illustrated in S501 of FIG. 5.

FIG. 6 is a view illustrating the example of detailed processing of a pre-sterilizing process illustrated in S501 of FIG. 5.

The processes (processing) illustrated in FIG. 6 are performed by executing programs readable by the operation processing unit 201 of the sterilizing apparatus 100 to control the operations of each device.

The processes (processing) illustrated in FIG. 6 are performed by the operation processing unit 201 of the sterilizing apparatus 100 which controls the operations of each device in the sterilizing apparatus.

First, in operation S601, the sterilizing apparatus 100 starts operating the gas feeding vacuum pump 220 and suctioning the gas in the sterilizing chamber 219.

Further, in operation S602, the sterilizing apparatus 100 determines whether the pressure (atmosphere) in the sterilizing chamber 219 is reduced to a predetermined atmosphere (for example, 45 Pa). More specifically, it is determined whether the pressure (atmosphere) in the sterilizing chamber 219 measured by a pressure sensor installed in the sterilizing chamber 219 is reduced to a predetermined atmosphere (for example, 45 Pa).

When it is determined in operation S602 that the pressure (atmosphere) in the sterilizing chamber 219 is not reduced to a predetermined atmosphere (for example, 45 Pa (NO in operation S602), the sterilizing apparatus 100 continues to operate the gas feeding vacuum pump 220, suctions the gas in the sterilizing chamber 219, and reduces the pressure (atmosphere) in the sterilizing chamber 219.

When it is determined in operation S602 that the pressure (atmosphere) in the sterilizing chamber 219 is reduced to a predetermined atmosphere (for example, 45 Pa (YES in operation S602), the sterilizing apparatus 100 continues to operate the gas feeding vacuum pump 220, suctions the gas in the sterilizing chamber 219, and starts processing of operation S502.

An example of detailed processing of sterilizing processing illustrated in S502 of FIG. 5 will be described with reference to FIGS. 7A through 7D.

Figure 7A:
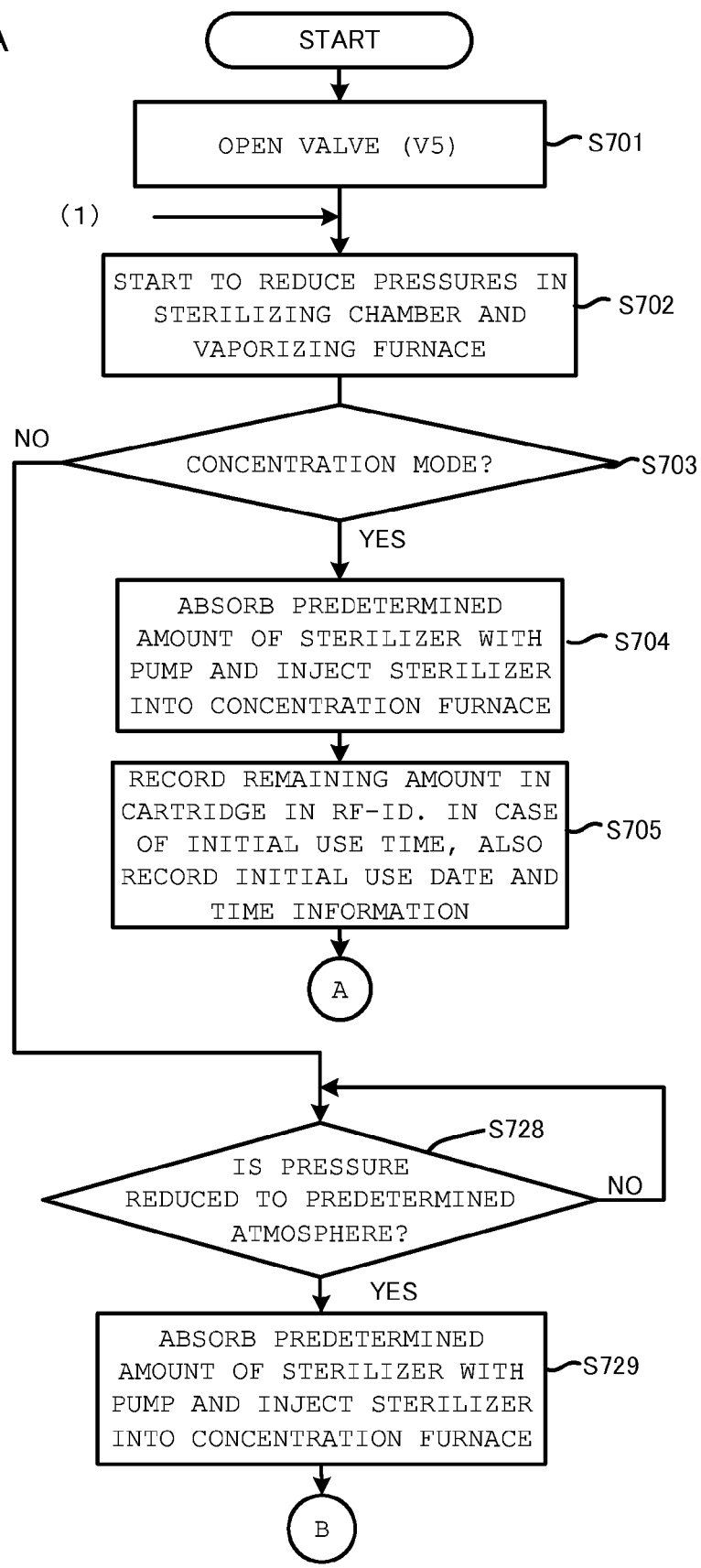
FIG. 7A is the first part of a flowchart illustrating an example of detailed processing of the sterilizing illustrated in S502 of FIG. 5.

FIG. 7A is the first part of a flowchart illustrating the example of detailed processing of a sterilizing process illustrated in S502 of FIG. 5.

The processes (processing) illustrated in FIGS. 7A through 7D are performed by executing programs readable by the operation processing unit 201 of the sterilizing apparatus 100 to control the operations of each device.

The processes (processing) illustrated in FIGS. 7A through 7D are performed by the operation processing unit 201 of the sterilizing apparatus 100 which controls the operations of each device in the sterilizing apparatus.

FIG. 7A is the first part of a flowchart illustrating the example of detailed processing of a sterilizing process illustrated in S502 of FIG. 5.

First, in operation S701, the sterilizing apparatus 100 opens the valve (V5) 217, and the sterilizing chamber 219 and the vaporizing furnace 216 in operation S701 communicate with each other through the conduit. Accordingly, currently, the gas in the sterilizing chamber 219 is suctioned and gas pressure is reduced by the gas feeding vacuum pump 220, and thus the pressures in the sterilizing chamber 219 and the vaporizing furnace 216 start to decrease in operation S702.

Then, the sterilizing apparatus 100 determines in operation S703 whether one of the button 304 for the 'mode of concentrating a sterilizer to perform sterilization' and the button 305 for the 'mode of performing sterilization without concentrating a sterilizer' is buttoned down in operation S110. When it is determined that the button 304 for the 'mode of concentrating a sterilizer to perform sterilization' is buttoned down (YES in operation S703), processing of operation S704 is performed. When it is determined that the button 305 for the 'mode of performing sterilization without concentrating a sterilizer' is buttoned down (NO in operation S703), processing of operation S728 is performed.

First, a case where the button 304 for the 'mode of concentrating a sterilizer to perform sterilization' is buttoned down (the sterilizer is concentrated to perform sterilization) will be described.

In operation S704, the sterilizing apparatus 100 operates the liquid feeding rotary pump 207 and absorbs a predetermined amount (for example, 2 millimeters) of sterilizer in the cartridge 205. Then, the predetermined amount of absorbed sterilizer is injected into the concentration furnace 208. The predetermined amount of sterilizer to be absorbed here is such an amount, for example, that the space in the sterilizing chamber 219 may be saturated with the sterilizer.

Then, in operation S705, the sterilizing apparatus 100 records the remaining amount of sterilizer left in the cartridge 205 in the RF-ID of the cartridge 205 attached to the attachment position. More specifically, a value obtained by subtracting a predetermined amount (for example, 2 milliliters) of sterilizer absorbed from the cartridge 205 in operation S704, from the remaining amount of a sterilizer in the cartridge 205 read in operation S101 is recorded in the RF-ID.

Further, when an initial use date and time (date and time when the cartridge is used in the sterilizing apparatus for the first time) read from the RF-ID in operation S101 does not contain information representing the date and time, the sterilizing apparatus 100 determines that the cartridge is used in the sterilizing apparatus for the first time at this time. In this way, only when it is determined that the cartridge is used in the sterilizing apparatus for the first time, current date and time information is also recorded in the RF-ID.

Figure 7B:
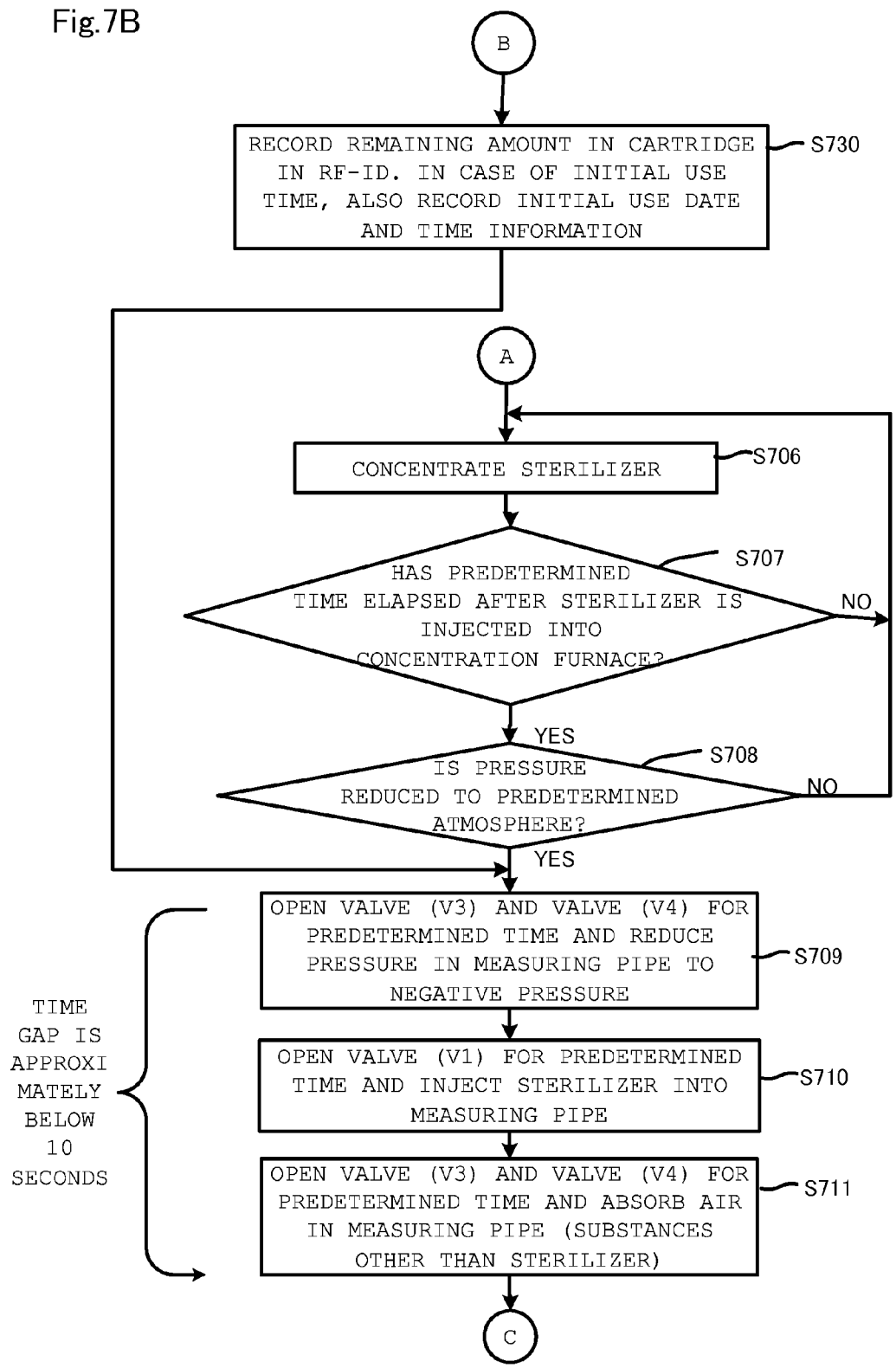
FIG. 7B is the second part of a flowchart illustrating an example of detailed processing of the sterilizing illustrated in S502 of FIG. 5.

Next, the sterilizing apparatus 100 always heats a heater installed in the concentration furnace 208 when a power source is turned on in the sterilizing apparatus 100, and thus the sterilizer injected into the concentration furnace 208 in operation S704 is heated by the heater, and leading to continuation connector A which continues in FIG. 7B, which evaporates moisture contained in the sterilizer in the concentration furnace 208 in operation S706.

FIG. 7B is the second part of a flowchart illustrating the example of detailed processing of a sterilizing process illustrated in S502 of FIG. 5.

From continuation connector A, the heater evaporates moisture contained in the sterilizer in the concentration furnace 208 in operation S706.

More specifically, when the sterilizer is hydrogen peroxide (also referred to as a hydrogen peroxide solution), the heater installed in the concentration furnace 208 is heated, specifically, for example, to 80 degrees here. Accordingly, it becomes possible to mainly evaporate (vaporize) moisture and concentrate the sterilizer.

Next, in operation S707, the sterilizing apparatus 100 determines whether a predetermined time (for example, 6 minutes) has elapsed after the sterilizer is injected into the concentration furnace 208 in operation S704. If it is determined that a predetermined time has elapsed after the sterilizer is injected into the concentration furnace 208 (YES in operation S707), processing of operation S708 is performed. Meanwhile, when a predetermined time has not elapsed after the sterilizer is injected into the concentration furnace 208 (NO in operation S707), the sterilizer continues to be concentrated while the sterilizer remains in the concentration furnace 208.

Next, in operation S708, the sterilizing apparatus 100 determines whether the pressure in the sterilizing chamber 219 and the vaporizing furnace 216 is reduced to a predetermined atmosphere (for example, 500 Pa).

When the pressure in the sterilizing chamber 219 and the vaporizing chamber 216 is reduced to a predetermined atmosphere (YES in operation S708), the sterilizing apparatus 100 opens the valve (V3) 212 and the valve (V4) 213 for a predetermined time (opens the valve (V3) 212 and the valve (V4) 213 for a predetermined time (for example, 3 seconds) and closes the valve (V3) 212 and the valve (V4) 213) to reduce the pressure in the measuring pipe 214. Meanwhile, when the pressures in the sterilizing chamber 219 and the vaporizing chamber 216 are not reduced to a predetermined atmosphere (NO in operation S708), the sterilizer continues to be concentrated. The process proceeds to continuation connector A.

Next, if the sterilizing apparatus 100 opens the valve (V3) 212 and the valve (V4) 213 for a predetermined time in operation S709, and closes the valve (V3) 212 and the valve (V4) 213 and opens the valve (V1) for a predetermined time (for example, 3 seconds) in operation S710, the pressure in the measuring pipe 214 is lower than the pressure of the concentration furnace (exterior) 208, and thus the sterilizer injected into the concentration furnace 208 is suctioned into the measuring pipe 214 in operation S710. By opening the valve (V1) for a predetermined time and closing the valve (V1), the sterilizer injected into the concentration furnace 208 is suctioned into the measuring pipe 214. The air in the concentration furnace 208 as well as the sterilizer is also suctioned into the measuring pipe 214.

Thereafter, a pressure in the sterilizing chamber 219 continues to be reduced by the gas feeding vacuum pump 220.

For this reason, the pressure in the sterilizing chamber 219 becomes lower than the pressure in the measuring pipe. Specifically, the pressure in the sterilizing chamber 219 is approximately 400 Pa, and the pressure in the measuring pipe is a value corresponding to approximately the atmospheric pressure (101325 Pa). The reason why the pressure in the measuring pipe is increased up to the vicinity of the atmospheric pressure is that the air in the concentration furnace 208 as well as the sterilizer is also suctioned into the measuring pipe 214.

Next, in operation S711, the sterilizing apparatus 100 opens the valve (V3) 212 and the valve (V4) 213 for a predetermined time (for example, 3 seconds), and suctions out the air in the measuring pipe (not containing the liquid sterilizer) to the sterilizing chamber 219. More specifically, if the valve (V3) 212 and the valve (V4) 213 are opened and the predetermined time elapses, the valve (V3) 212 and the valve (V4) 213 are closed. The process proceeds to continuation connector C which continues in FIG. 7C.

Figure 7C:
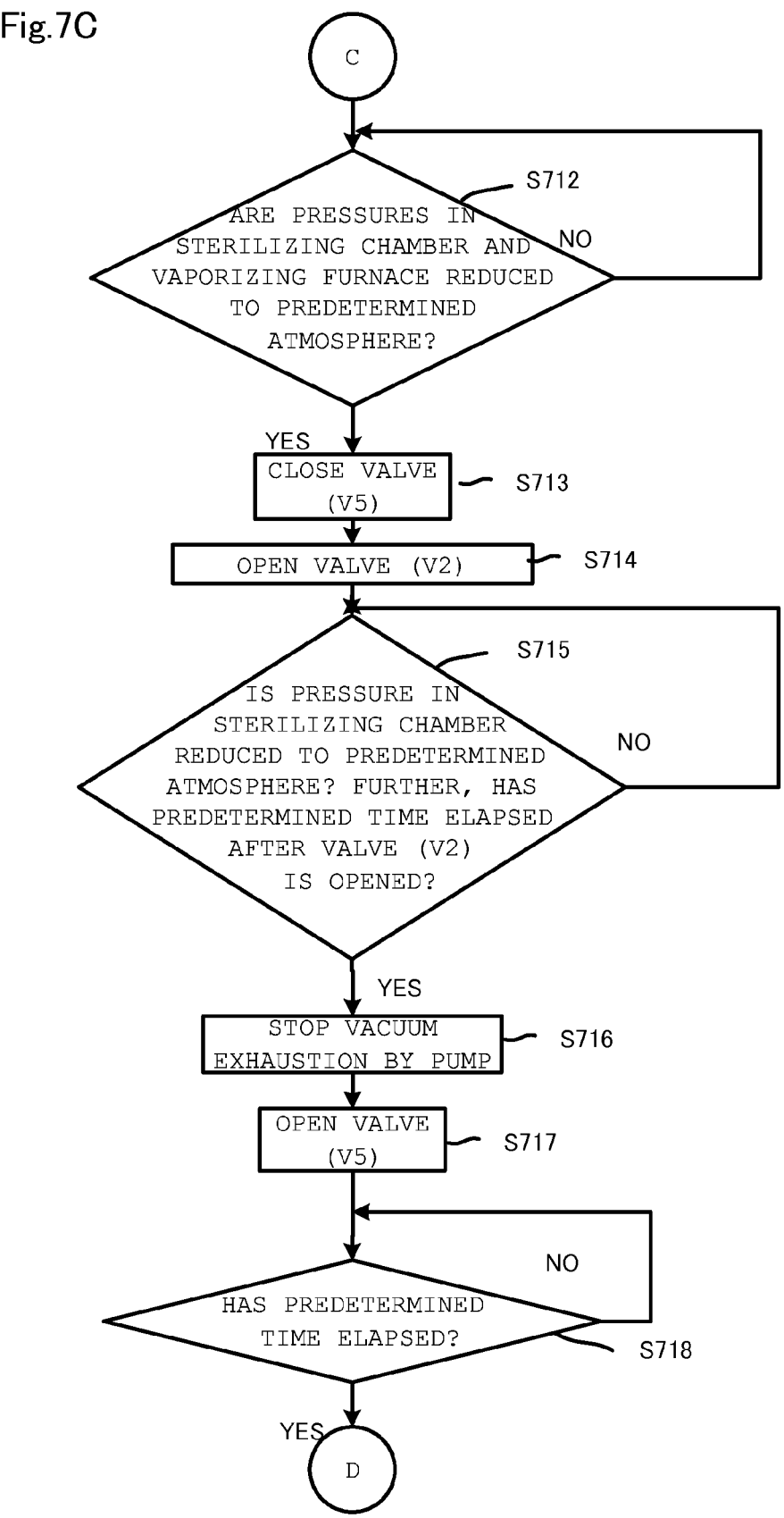
FIG. 7C is the third part of a flowchart illustrating an example of detailed processing of the sterilizing illustrated in S502 of FIG. 5.

FIG. 7C is the third part of a flowchart illustrating the example of detailed processing of a sterilizing process illustrated in S502 of FIG. 5.

Next, the sterilizing apparatus 100 determines whether the pressure in the sterilizing chamber 219 and the vaporizing chamber 216 is reduced to a predetermined atmosphere (for example, 80 Pa), and when it is determined that the pressure is reduced in operation S712, the valve (V5) 217 is closed in operation S713.

Further, the sterilizing apparatus 100 opens the valve (V2) 215 in operation S714. Accordingly, the sterilizer in the measuring pipe 214 is suctioned into the vaporizing furnace 216 and is vaporized in the vaporizing furnace 216.

The sterilizer is vaporized in the vaporizing furnace as a molecular cluster.

The interior of the sterilizing chamber has a cubic capacity larger than that of the vaporizing furnace, and the sterilizer is vaporized as molecule clusters. It is because the capacity of the vaporizing furnace is smaller than that of the sterilizing chamber, and the distances between the molecules of the sterilizer in the sterilizing chamber is closer, so that the molecular cluster may be easily formed by the molecular force.

Even in this case, the gas feeding vacuum pump 220 continues to suction the gas in the sterilizing chamber 219 and reduces the pressure in the sterilizing chamber 219. The atmospheric pressure within the vaporizing furnace 216 which suctions the sterilizer in the measuring pipe 214 increases. In other words, the pressure in the vaporizing furnace 216 becomes higher than the pressure in the sterilizing chamber 219.

Next, the sterilizing apparatus 100 determines in operation S715 whether a predetermined time has elapsed after the pressure in the sterilizing chamber 219 is reduced to a predetermined atmosphere (for example, 50 Pa) and the valve (V2) 215 is opened in operation S714, and when the pressure in the sterilizing chamber 219 is reduced to a predetermined atmosphere (for example, 50 Pa) and a predetermined time has elapsed after the valve (V2) 215 is opened in operation S714 (YES in operation S715), a suctioning (vacuuming) operation of the sterilizing chamber 219 by the gas feeding vacuum pump 220 is stopped in operation S716 and the valve (V5) 217 is opened in operation S717. Accordingly, the sterilizer vaporized in the sterilizing chamber 219 may be diffused to sterilize the sterilize target.

The sterilizer is diffused because the pressure (for example, 50 Pa) in the sterilizing chamber 219 is lower than the pressure in the vaporizing furnace 216.

The molecular cluster of the diffused sterilizer in the vaporizing furnace is further broken up, and thus the sterilizer may be further diffused in the sterilizing chamber, which enhances a sterilizing action.

Further, a cavity of the sterilize object may be effectively sterilized.

Figure 7D:
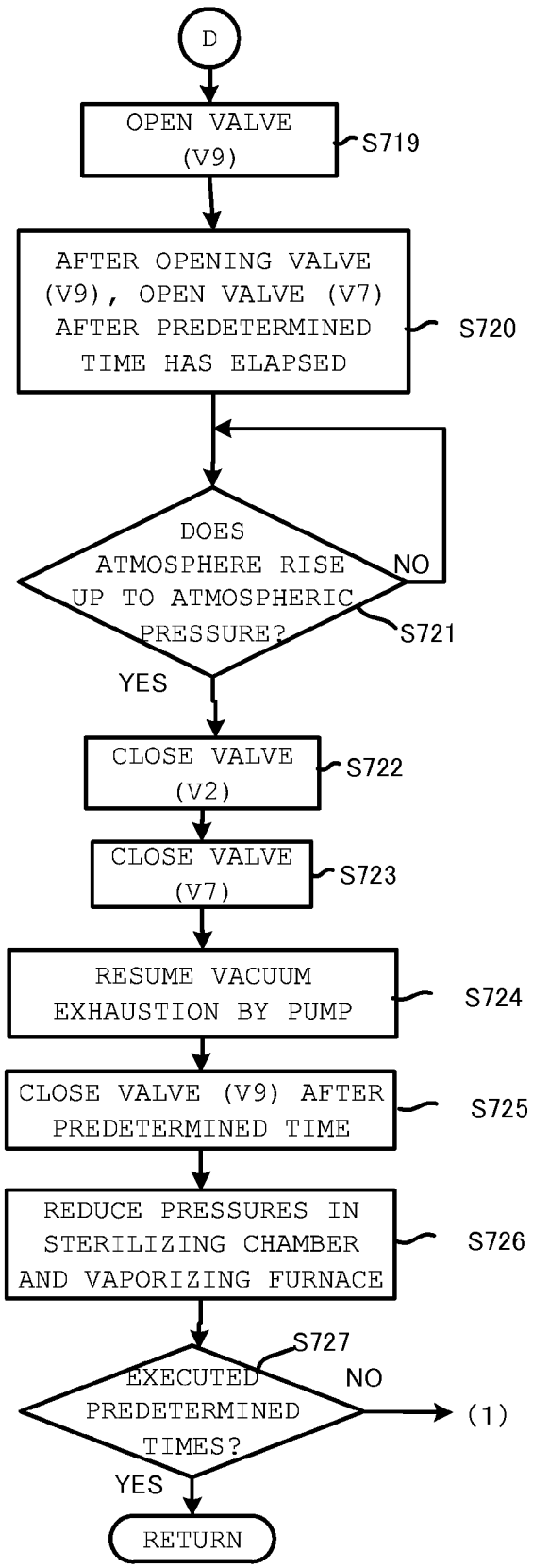
FIG. 7D is the fourth part of a flowchart illustrating an example of detailed processing of the sterilizing illustrated in S502 of FIG. 5.

Further, it is determined in operation S717 whether a predetermined time (for example, 330 seconds) has elapsed after the valve (V5) 217 is opened, and if it is determined that a predetermined time (for example, 330 seconds) has elapsed after the valve (V5) 217 is opened (YES in operation S718), the valve (V9) 227 is opened in operation S719 as shown in FIG. 7D.

Accordingly, the pressure in the vaporizing furnace 216 and the sterilizing chamber 219 is lower than the atmosphere outside the sterilizing apparatus 100, and thus the external air (atmosphere) outside the sterilizing apparatus 100 cleaned in the gas suctioning HEPA filter is suctioned into the vaporizing furnace 216. Further, the sterilizer remaining in the vaporizing furnace 216 as a gas and the sterilizer attaching to a surface of the interior of the vaporizing furnace 216 are fed into the sterilizing chamber 219 by the air brought into the vaporizing furnace 216. Accordingly, a sufficient amount of gasified sterilizer is fed into the sterilizing chamber 219, and a sterilizing action on the sterilize target present in the sterilizing chamber 219 is enhanced.

In addition, for example, a sterilizing action on a cavity is enhanced because the atmosphere fed in later forces the gasified sterilizer because even into a sterilize object having a part (cavity) which may not be easily sterilized through the processing, such as a deep part of a thin tube of the sterilize object. More specifically, the vaporizing chamber 216 is vacuumed by the gas feeding vacuum pump 220 (vacuum device) which is a feature of an embodiment, after the gasified sterilizer (sterilizer gas) vaporized in the vaporizing chamber is injected into the sterilizing chamber 219. The vaporizing chamber 216 and the atmosphere communicate with each other by opening the valve (V9) 227 (first atmosphere opening valve) while the vaporizing chamber 216 and the sterilizing chamber 219 communicate with each other. Accordingly, the sterilizer left in the vaporizing chamber for gasifying the sterilizer may be fed into the sterilizing chamber, and a sufficient sterilizing action may be stimulated. The process proceeds to continuation connector D which continues in FIG. 7D.

FIG. 7D is the fourth part of a flowchart illustrating the example of detailed processing of a sterilizing process illustrated in S502 of FIG. 5.

From continuation connector D, in operation S719, if a predetermined time (15 seconds) has elapsed after the valve (V9) 227 is opened, the sterilizing apparatus 100 opens the valve (V7) 226 (corresponding to the second atmosphere opening valve of an embodiment), and the external air (atmosphere) outside the sterilizing apparatus 100 cleaned by the gas suctioning HEPA filter 210 is suctioned into the sterilizing chamber 219. This is because the pressure in the sterilizing chamber 219 and the vaporizing furnace 216 is lower than the atmosphere outside the sterilizing apparatus 100, and thus the external air (atmosphere) outside the sterilizing apparatus 100 is suctioned into the sterilizing chamber 219.

More specifically, the first atmosphere opening valve is opened to communicate the vaporizing chamber with the atmosphere and then the second atmosphere opening valve is opened to communicate the sterilizing chamber with the atmosphere while the vaporizing chamber and the sterilizing chamber communicate with each other, the sterilizer may be more strongly forced into a cavity by feeding the sterilizer left in the vaporizing chamber into the sterilizing chamber, and injecting the sterilizer into the sterilizing chamber and then an amount of atmosphere injected per predetermined time is increased.

In addition, according to the present exemplary embodiment, the vaporizing chamber and the atmosphere communicate with each other when the first atmosphere opening valve is opened, and the sterilizing chamber and the atmosphere communicate with each other when the second atmosphere opening valve is opened after a predetermined time. However, the sterilizing chamber and the atmosphere may communicate with each other when the second atmosphere opening valve is opened after a pressure in the sterilizing chamber reaches a predetermined pressure. In any case, an effect of bringing in the sterilizer may be increased by opening the first atmosphere opening valve, opening the second atmosphere opening valve, and suctioning a large amount of atmosphere, and an effect of sterilizing a cavity of the sterilize object having the cavity may be increased.

Next, the sterilizing apparatus 100 determines whether the pressure in the sterilizing chamber 219 and the vaporizing furnace 216 has increased up to the atmospheric pressure, and when it is determined that the pressure has increased up to the atmospheric pressure (YES in operation S721), the valve (V2) 215 is closed in operation S722.

Next, the sterilizing apparatus 100 closes the valve (V7) 226 in operation S723, and resumes a suctioning (vacuuming) operation within the sterilizing chamber 219 by the gas feeding vacuum pump 220 in operation S724. Accordingly, the external air (atmosphere) outside the sterilizing apparatus 100 cleaned by the gas suctioning HEPA filter 210 is suctioned into the vaporizing furnace 216 through a conduit with which the gas suctioning HEPA filter 210 and the vaporizing furnace 216 communicate. Further, the sterilizer filling the vaporizing furnace 216 as a gas and the sterilizer attaching to a surface of the interior of the vaporizing furnace 216 are fed into the sterilizing chamber 219 by the air fed into the vaporizing furnace 216.

Accordingly, a sterilizing action on a part (in particular, a cavity part) which may not be easily sterilized, such as a deep point of a thin tube of the sterilize object, is enhanced, and the sterilizer in the vaporizing furnace 216 may be effectively reduced.

Then, after resuming a suctioning (vacuuming) operation within the sterilizing chamber 219 by the gas feeding vacuum pump 220 in operation S724, the sterilizing apparatus 100 closes the valve (V9) 227 after a predetermined time (for example, 15 seconds) has elapsed in operation S725.

Even in this case, a suctioning (vacuuming) operation within the sterilizing chamber 219 by the gas feeding vacuum pump 220 is continued, and the interiors of the sterilizing chamber 219 and the vaporizing furnace 216 are sealed in operation S725, and the pressure in the sterilizing chamber 219 and the vaporizing chamber 216 is reduced in operation S726.

Next, the sterilizing apparatus 100 determines in operation S727 whether operation S702 to operation S726 are performed predetermined times (for example, four times) in operation S727, and when it is determined that the steps are performed (YES in operation S727), processing of operation S503 is performed. Meanwhile, when it is determined that the processing of operation S702 and operation S726 are not performed predetermined times, processing after operation S702 is performed again. In this way, as the processing of operation S702 to operation S726 are performed the predetermined times, a sterilizing effect on the sterilize object increases, and the sterilize object may be sufficiently sterilized.

Next, a case where it is determined that the button 305 for the 'mode of performing sterilization without concentrating a sterilizer' is buttoned down (a sterilization is performed without concentrating the sterilizer) in operation S703 will be described.

When it is determined that the button 305 for the 'mode of performing sterilization without concentrating a sterilizer' is buttoned down (NO in operation S703), it is determined whether the pressure in the sterilizing chamber 219 and the vaporizing furnace 216 is reduced to a predetermined atmosphere (for example, 1000 Pa) in operation S728.

If it is determined that the pressure in the sterilizing chamber 219 and the vaporizing chamber 216 is reduced to a predetermined atmosphere (for example, 100 Pa) (YES in operation S728), the liquid feeding rotary pump 207 is operated, and the sterilizer in the cartridge 205 is absorbed by a predetermined amount (for example, 2 milliliters). In addition, the predetermined amount of absorbed sterilizer is injected into the concentration furnace 208 in operation S729.

The predetermined amount of sterilizer absorbed here is an amount, for example, by which the space in the sterilizing chamber 219 is saturated with the sterilizer. The process proceeds to continuation connector B which continues in FIG. 7B.

Refer to FIG. 7B, from continuation connector B shown in FIG. 7A, in operation S730, the sterilizing apparatus 100 records the remaining amount of sterilizer left in the cartridge 205 in the RF-ID of the cartridge 205 attached to the attachment position of the cartridge. More specifically, a value obtained by subtracting a predetermined amount (for example, 2 milliliters) of sterilizer absorbed from the cartridge 205 in operation S729 from the remaining amount of sterilizer in the cartridge 205 read in operation S101 is stored in the RF-ID.

Further, in operation S730, when an initial use date and time (date and time when the cartridge is used in the sterilizing apparatus for the first time) read from the RF-ID in operation S101 does not contain information representing the date and time, the sterilizing apparatus 100 determines that the cartridge is used in the sterilizing apparatus for the first time at this time. In this way, only when it is determined that the cartridge is used in the sterilizing apparatus for the first time, current date and time information is also recorded in the RF-ID.

Further, if the processing of operation S730 is performed, the sterilizing apparatus 100 performs the processing after the above-described operation S709.

If a pressure in the sterilizing chamber 219 becomes a predetermined atmosphere (for example, 1000 Pa) in operation S728, the sterilizer starts to be absorbed in operation S729 and the pressure is below 500 Pa when all the sterilizer is absorbed in operation S729, the processing may be efficiently shifted to operation S709.

In this way, after the pressure in the sterilizing chamber 219 and the vaporizing chamber 216 is reduced to a predetermined atmosphere (for example, 1000 Pa) at which a pressure in the measuring pipe 214 starts to be reduced, a predetermined amount of absorbed sterilizer may be injected into the concentration furnace 208. Accordingly, a pressure in the measuring pipe 214 may be reduced immediately in operation S709, and then the sterilizer in the concentration furnace 208 is injected into the measuring pipe in operation S710, the sterilizer may be immediately injected from the concentration furnace 208 into the measuring pipe 214. In other words, the sterilizer may be injected into the measuring pipe 214 without being concentrated in the concentration furnace 208.

An example of detailed processing of a ventilating processing illustrated in S503 of FIG. 5 will be described with reference to FIGS. 8A and 8B.

Figure 8A:
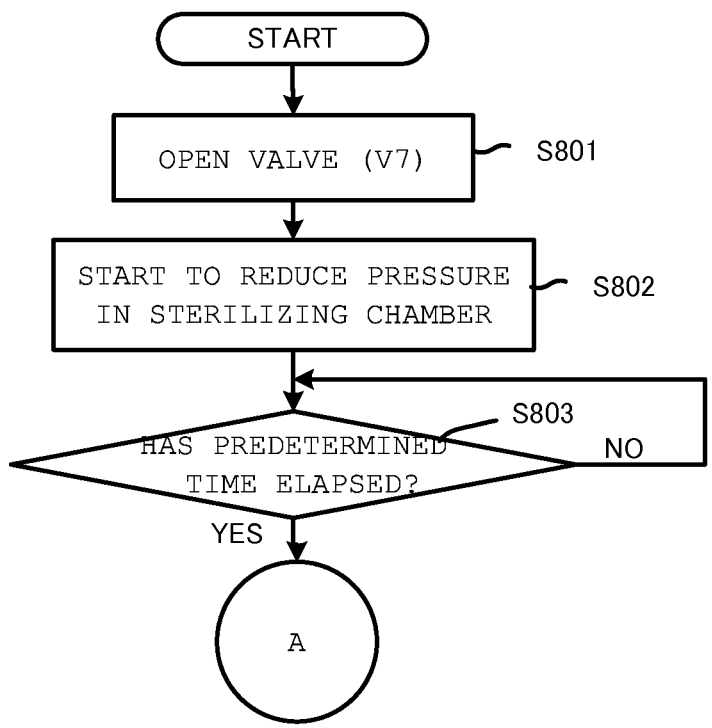
FIG. 8A is the first part of a flowchart illustrating an example of detailed processing of a ventilating process illustrated in S503 of FIG. 5.

FIG. 8A is the first part of a flowchart illustrating the example of detailed processing of a ventilating process illustrated in S503 of FIG. 5.

Figure 8B:
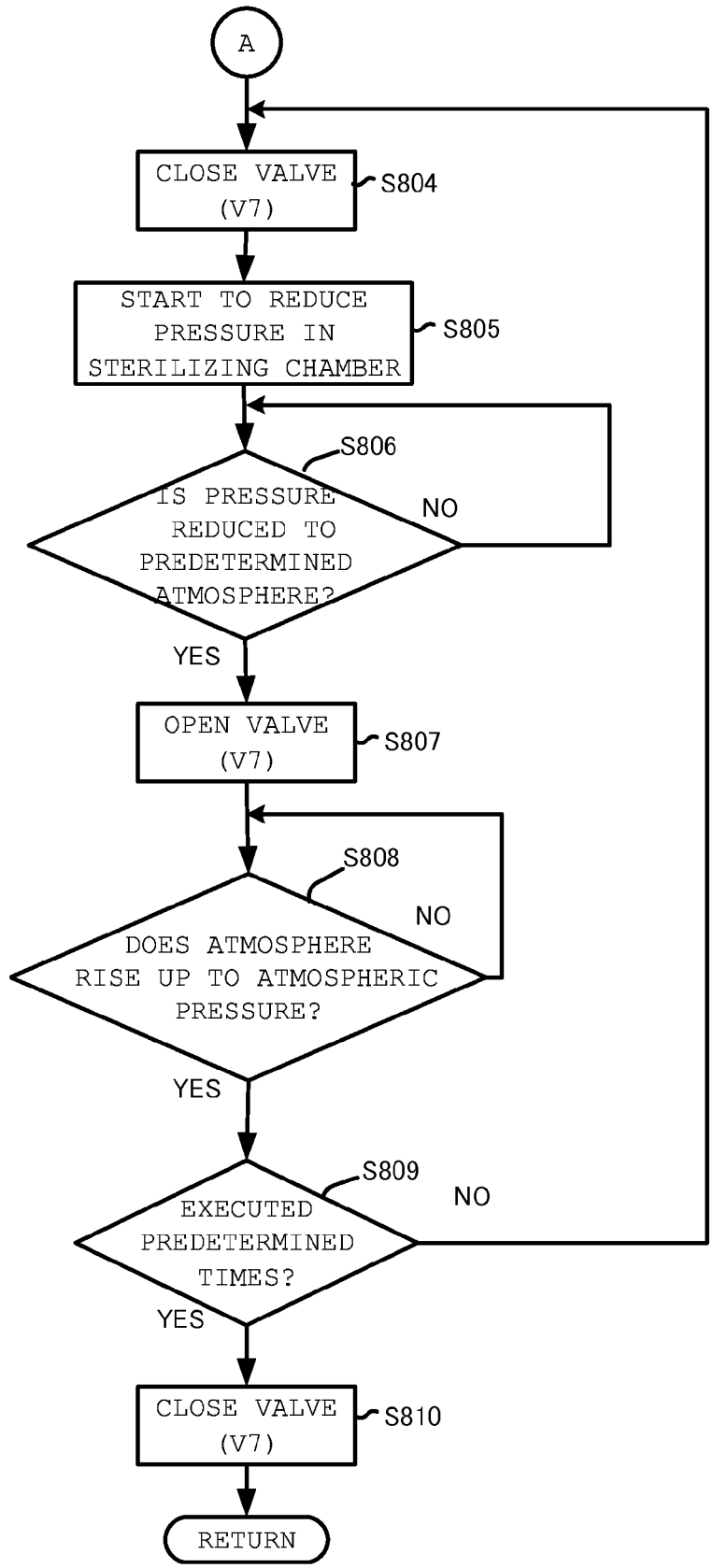
FIG. 8B is the second part of a flowchart illustrating an example of detailed processing of a ventilating process illustrated in S503 of FIG. 5.

The processes (processing) illustrated in FIGS. 8A and 8B are performed by the operation processing unit 201 of the sterilizing apparatus 100 which controls the operations of the units in the sterilizing apparatus.

More specifically, the processes (processing) illustrated in the drawings are performed by executing programs readable by the operation processing unit 201 of the sterilizing apparatus 100 to control the operations of each device.

First, the sterilizing apparatus 100 opens the valve (V7) 226 in operation S801.

Further, the sterilizing apparatus 100 continues a suctioning (vacuuming) operation within the sterilizing chamber 219 by the gas feeding vacuum pump 220 in operation S802.

If a predetermined time has elapsed (YES in operation S803) after the valve (V7) 226 is opened in operation S801 and a suctioning (vacuuming) operation is performed within the sterilizing chamber 219 by the gas feeding vacuum pump 220 in operation S802, the process proceeds to continuation connector A which continues in FIG. 8B.

FIG. 8B is the second part of a flowchart illustrating the example of detailed processing of a ventilating process illustrated in S503 of FIG. 5.

From continuation connector A, the valve (V7) 226 is closed in operation S804, and a suctioning (vacuuming) operation within the sterilizing chamber 219 by the gas feeding vacuum pump 220 is continuously performed. Accordingly, the pressure in the sterilizing chamber 219 is reduced in operation S805.

Next, if the pressure in the sterilizing chamber 219 is reduced to a predetermined atmosphere 50 Pa (YES in operation S806), the sterilizing apparatus 100 opens the valve (V7) 226 (step S807). Accordingly, the external air (atmosphere) outside the sterilizing apparatus 100 cleaned by the gas suctioning HEPA filter 210 is suctioned into the sterilizing chamber 219. This is because the pressure in the sterilizing chamber 219 is lower than the atmosphere outside the sterilizing apparatus 100, and thus the external air (atmosphere) outside the sterilizing apparatus 100 is suctioned into the sterilizing chamber 219.

It is determined whether the pressure in the sterilizing chamber 219 has increased up to the atmospheric pressure. If it is determined that the pressure in the sterilizing chamber 219 has increased up to the atmospheric pressure (YES in operation S808), the sterilizing apparatus 100 determines whether the processing of operation S804 to operation S808 has been performed predetermined times (for example, four times) in operation S809. If the processing of operation S804 to operation S808 has been performed predetermined times (for example, four times) (YES in operation S809), the valve (V7) 226 is closed in operation S810 and the ventilating process is ended.

Meanwhile, when the processing of operation S804 to operation S808 has not been performed predetermined times (for example, four times) (NO in operation S809), the processing starts from operation S804 again.

Accordingly, the sterilizer attaching to a surface of the interior of the sterilizing chamber 219 and the sterilizer left in the sterilizing chamber 219 as a gas are suctioned by the gas feeding vacuum pump 220. The suctioned gas (containing the sterilizer) passes through the gas exhausting HEPA filter 221, the sterilizer is decomposed by the sterilizer decomposing unit 222, and the decomposed molecules are discharged to the outside.

Next, an example of detailed processing of the sterilizing processing illustrated in S114 of FIG. 4 will be described with reference to FIG. 9.

Figure 9:
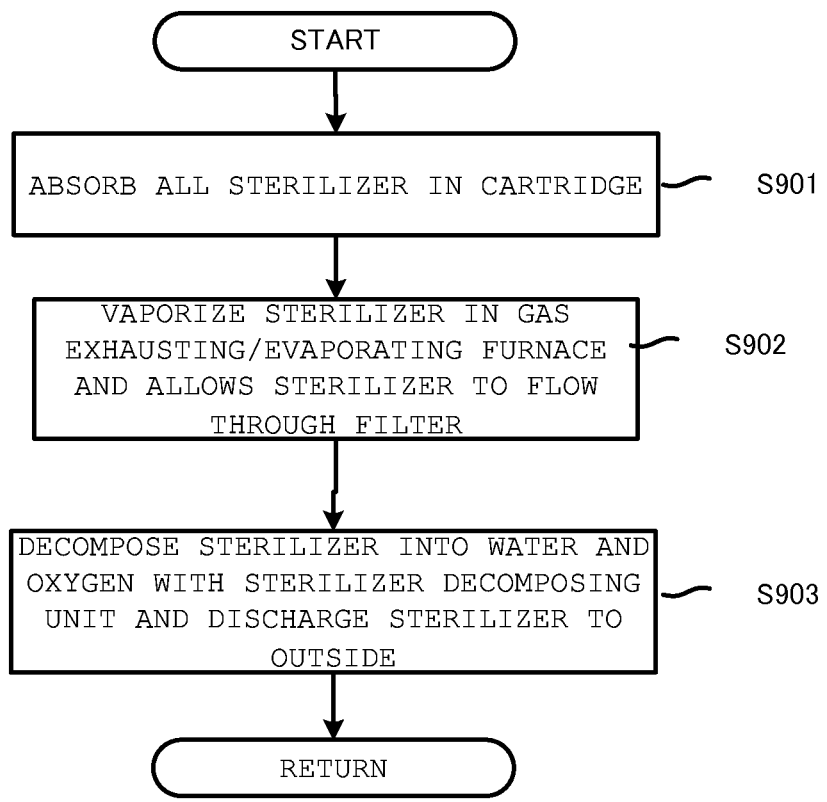
FIG. 9 is a view illustrating an example of detailed processing of the sterilizer discharging illustrated in S114 of FIG. 4B.

FIG. 9 is a view illustrating the example of detailed processing of the sterilizer discharging processing illustrated in S114 of FIG. 4.

The processes (processing) illustrated in FIG. 9 are performed by the operation processing unit 201 of the sterilizing apparatus 100 which controls the operations of each device in the sterilizing apparatus.

In other words, the processes (processing) illustrated in FIG. 9 are performed by executing programs readable by the operation processing unit 201 of the sterilizing apparatus 100 to control the operations of each device.

First, in the sterilizing apparatus 100, the liquid feeding rotary pump 223 suctions all the liquid sterilizer in the cartridge 205 with a pump, and feeds all the sterilizer sent through the conduit between the liquid sensor 204 and the liquid feeding rotary pump 223 to the gas exhausting/evaporating furnace 224 through the conduit between the liquid feeding rotary pump 223 and the gas exhausting/evaporating furnace 224 in operation S901.

Further, in the sterilizing apparatus 100, the gas exhausting/evaporating furnace 224 heats all the liquid sterilizer fed through the conduit between the liquid feeding rotary pump 223 and the gas exhausting/evaporating furnace 224 with a heater disposed in the gas exhausting/evaporating furnace 224, and evaporates all the sterilizer. The evaporated sterilizer is fed to the gas exhausting HEPA filter 221 through the conduit between the gas exhausting HEPA filter 221 and the gas exhausting/evaporating furnace 224 in operation S902.

The heater installed in the gas exhausting/evaporating furnace 224 is heated to a temperature higher than, for example, a boiling point (a boiling point of hydrogen peroxide is 141 degrees) of the sterilizer (hydrogen peroxide). For this reason, all the sterilizer is vaporized by the gas exhausting/evaporating furnace 224.

The sterilizing apparatus 100 cleans the vaporized sterilizer sent through a conduit between the gas exhausting/evaporating furnace 224 and the gas exhausting HEPA filter 221, with the gas exhausting HEPA filter 221, and the cleaned gas (containing the sterilizer) is sent to the sterilizer decomposing unit 222 through a conduit between the sterilizer decomposing unit 222 and the gas exhausting HEPA filter 221.

The sterilizer decomposing unit 222 decomposes the molecules of the sterilizer contained in the gas sent from the conduit between the sterilizer decomposing unit 222 and the gas exhausting HEPA filter 221, and emits the molecules produced through the decomposition to the outside of the sterilizing apparatus 100 in operation S903.

A block diagram of a hardware configuration including a concentration furnace 208, a valve (V1) 211, a valve (V3) 212, a valve (V4) 213, a measuring pipe 214, a valve (V2) 215, a vaporizing furnace 216, a valve (V5) 217, a valve (V9) 227 of the sterilizing apparatus 100 according to an embodiment will be described with reference to FIG. 10.

Figure 10:
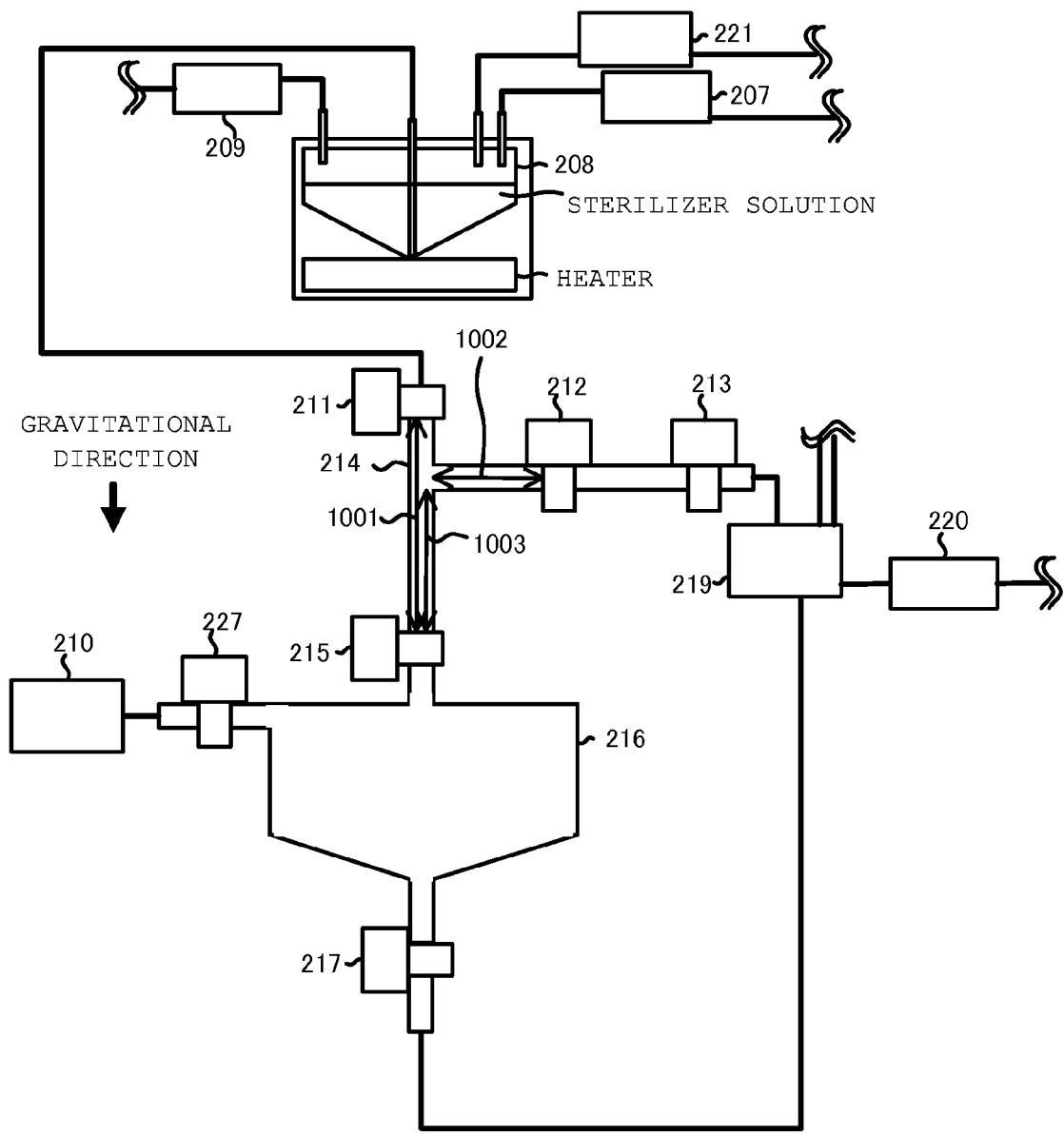
FIG. 10 is a view illustrating an example of a block diagram showing a hardware configuration of a concentration furnace, a valve (V1), a valve (V3), a valve (V4), a measuring pipe, a valve (V2), a vaporizing furnace, a valve (V5), and a valve (V9) of the sterilizing apparatus according to an embodiment.

FIG. 10 is a view illustrating an example of a block diagram of a hardware configuration including a concentration furnace 208, a valve (V1) 211, a valve (V3) 212, a valve (V4) 213, a measuring pipe 214, a valve (V2) 215, a vaporizing furnace 216, a valve (V5) 217, a valve (V9) 227 of the sterilizing apparatus 100 according to an embodiment.

The hardware of FIG. 10 which is the same as the hardware illustrated in FIG. 2 is denoted by the same reference numeral.

In operation S704 and operation S729, the sterilizing apparatus 100 operates the liquid feeding rotary pump 207 and absorbs a predetermined amount (for example, 2 milliliters) of sterilizer in the cartridge 205, and injects the predetermined amount of absorbed sterilizer into the concentration furnace 208.

In operation S706, as illustrated in FIG. 10, a heater is installed at a lower portion of the concentration furnace 208, and the sterilizer is heated by the heater. When the sterilizer is a hydrogen peroxide solution, water is vaporized by the heat of the heater. Further, the vaporized water is forced out to a conduit communicating with the gas exhausting HEPA filter 221, by the air fed through a conduct from the gas feeding/pressurizing pump 209, and is exhausted from the concentration furnace 208. Accordingly, the sterilizer (a hydrogen peroxide solution) is concentrated.

As described in FIG. 7, in operation S710, the sterilizer in the concentration furnace 208 is injected into the measuring pipe 214.

As illustrated in FIG. 10, the measuring pipe 214 includes a straight pipe part 1001 and a branch pipe part 1002.

The linear pipe part 1001 is a linear pipe-shaped part. The pipe of the straight pipe part 1001 is disposed in a gravitational direction.

Further, the branch pipe part 1002 is a pipe-shaped part extending from a middle portion or an upper portion of the straight pipe part 1001 in a branch shape.

The straight pipe part 1001 is installed such that an axial center of the straight pipe part and an axial center of the branch pipe part 1002 are perpendicular to each other.

With this configuration, the sterilizer injected from the concentration furnace 208 remains in the straight pipe part 1001 in the measuring pipe 214. The part where the sterilizer remains in the straight pipe part 1001 is referred to as a sterilizer storage part 1003.

In other words, the sterilizer storage part 1003 has a sufficient space to store the sterilizer injected from the concentration furnace 208.

For this reason, the sterilizer injected from the concentration furnace 208 remains in the sterilizer storage part 1003, and the air injected from the concentration furnace 208 together with the sterilizer fills a space other than the space of the sterilizer remaining in the sterilizer storage part 1003. More specifically, the space other than the space for the sterilizer, is a space in the straight pipe part 1002 and is a space communicating with the space in the straight pipe part 1002, and thus the air is absorbed into the sterilizing chamber 219 by opening the valve (V3) 212 and the valve (V4) 213 in operation S711.

By opening the valve (V2) in operation S714, the sterilizer remaining in the sterilizer storage part 1003 is suctioned into the vaporizing furnace 216 and vaporized. As illustrated in FIG. 10, since the liquid sterilizer is injected into the vaporizing furnace 216 from the upper side of the vaporizing furnace 216, the sterilizer may be easily vaporized.

As illustrated in FIG. 10, a conduit between the gas suctioning HEPA filter 210 and the vaporizing furnace 216 is installed at an upper portion of the vaporizing furnace 216. Therefore, when the valve V9 is opened in operation S719, air (an exterior gas) is discharged from an upper portion of the vaporizing furnace 216 to the sterilizing chamber 219 located at a lower portion of the vaporizing furnace 216. Accordingly, the sterilizer attaching to the interior of the vaporizing furnace 216 and the vaporized sterilizer in the vaporizing furnace 216 may be easily removed in a wide range, and more of removed sterilizer may flow into the sterilizing chamber 219.

More specifically, the sterilizing apparatus for sterilizing an object is configured to include a sterilizing chamber which is a vacuum chamber for receiving an object; a vaporizing chamber configured to vaporize a sterilizer before the sterilizer is injected into the sterilizing chamber; a vacuum device configured to vacuum the sterilizing chamber and the vaporizing chamber; and a first atmosphere opening valve configured to perform an opening/closing operation to control communication between the vaporizing chamber and the atmosphere. After the sterilizer gas vaporized in the vaporizing chamber is injected into the sterilizing chamber by vacuuming the vaporizing chamber with the vacuum device, the vaporizing chamber and the atmosphere communicate with each other when the first atmosphere opening valve is opened while the vaporizing chamber and the sterilizing chamber communicate with each other. Accordingly, the sterilizing apparatus provides a structure for feeding a sterilizer left in a vaporizing chamber configured to gasify the sterilizer, into a sterilizing chamber and stimulating a sterilizing action while reducing waste of the sterilizer.

Further, the sterilizing apparatus is configured to include a second atmosphere opening valve configured to perform an opening/closing operation to control communication between the sterilizing chamber and the atmosphere. After the sterilizer gas vaporized in the vaporizing chamber is injected into the sterilizing chamber by vacuuming the vaporizing chamber with the vacuum device, the vaporizing chamber and the atmosphere communicate with each other when the first atmosphere opening valve is opened while the vaporizing chamber and the sterilizing chamber communicate with each other. Then, the sterilizing chamber and the atmosphere communicate with each other when the second atmosphere opening valve is opened. Accordingly, an effect of forcing the sterilizer into a cavity may be enhanced by feeding the sterilizer left in the vaporizing chamber into the sterilizing chamber and increasing an amount of atmosphere injected per predetermined time after the sterilizer is injected into the sterilizing chamber.

While the disclosure has been described with reference to exemplary embodiments, it is to be understood that the disclosure is not limited to the disclosed exemplary embodiments. The scope of the following claims is to be accorded the broadest interpretation so as to encompass all modifications, equivalent structures, and functions.

This application claims priority from Japanese Patent Application No. 2011-222381 filed Oct. 6, 2011, which is hereby incorporated by reference herein in its entirety.

What is claimed is:

1. A sterilizing method in a sterilizing apparatus which includes a sterilizing chamber for placing an object, a vacuum device configured to vacuum the sterilizing chamber and a vaporizing chamber, the vaporizing chamber configured to vaporize a liquid sterilizer to obtain sterilizer gas which is to be injected into the sterilizing chamber, wherein the liquid sterilizer is sent to the vaporizing chamber which has been subjected to the vacuuming by the vacuum device and within which a pressure is lower than an atmospheric pressure, to thereby cause the vaporizing chamber to vaporize the liquid sterilizer, a valve configured to perform an opening/closing operation to control communication between the vaporizing chamber and the sterilizing chamber, and a first atmosphere opening valve configured to perform an opening/closing operation to control communication between the vaporizing chamber and the atmosphere, the method comprising:

controlling the valve and the first atmosphere opening valve; and sterilizing the object by injecting the sterilizer gas into the sterilizing chamber vacuumed by the vacuum device, comprising:

causing the vacuum device to perform the vacuuming while the valve is in an opened state to reduce pressure within the sterilizing chamber and pressure within the vaporizing chamber;

causing the vaporizing chamber to vaporize the liquid sterilizer by closing the valve in a state in which the pressure in an inner part of the sterilizing chamber and the pressure in an inner part of the vaporizing chamber are reduced to a predetermined pressure lower than the atmospheric pressure and sending the liquid sterilizer to the vaporizing chamber without opening the first atmosphere opening valve;

injecting the sterilizer gas, obtained by vaporizing the liquid sterilizer in the vaporizing chamber into the sterilizing chamber by opening the valve thereafter without opening the first atmosphere opening valve;

secondarily injecting the sterilizer gas by opening the first atmosphere opening valve while maintaining the valve opened so as to cause the sterilizing apparatus to feed the atmosphere via the vaporizing chamber into the sterilizing chamber and thereby causing the atmosphere to bring in the sterilizer gas in the vaporizing chamber toward the inner part of the sterilizing chamber.

2. The sterilizing method according to claim 1, wherein the sterilizing apparatus further includes a second atmosphere opening valve configured to perform an opening/closing operation to control communication between the sterilizing chamber and the atmosphere, the method further comprising:

controlling the second atmosphere opening valve; and wherein sterilizing the object further comprises:
  opening the second atmosphere opening valve so as to cause the object to be further sterilized by the atmosphere being fed into the sterilizing chamber.

3. The sterilizing method according to claim 2, wherein opening the second atmosphere opening valve comprises:
  causing the object to be further sterilized by the atmosphere being fed into the sterilizing chamber after a predetermined time has elapsed since the first atmosphere opening valve has been opened.

4. The sterilizing method according to claim 2, wherein opening the second atmosphere opening valve comprises:
  causing the object to be further sterilized by the atmosphere being fed into the sterilizing chamber in a case where the sterilizing apparatus determines that the pressure within the sterilizing chamber has reached the predetermined pressure.

5. The sterilizing method according to claim 1, wherein sterilizing the object further comprises:
  in response to the pressure within the sterilizing chamber having reached the atmosphere, vacuuming the sterilizing chamber while the valve is maintained opened and closing the first atmosphere opening valve so as to thereby repeat the sterilizing a predetermined number of times.

6. The sterilizing method according to claim 1, wherein the liquid sterilizer is hydrogen peroxide.

* * * * *